(12) United States Patent
Iqbal et al.

(10) Patent No.: US 12,402,812 B1
(45) Date of Patent: Sep. 2, 2025

(54) FINGERPRINT RECOGNITION SYSTEM AND METHOD THEREFOR

(71) Applicant: Technology Control Company, Riyadh (SA)

(72) Inventors: Shahzaib Iqbal, Riyadh (SA); Tariq Khan, Riyadh (SA); Bandar Alshammari, Riyadh (SA); Bandar Alhaqbani, Riyadh (SA); Muhammad Imran, Riyadh (SA)

(73) Assignee: TECHNOLOGY CONTROL COMPANY, Riyadh (SA)

( * ) Notice: Subject to any disclaimer, the term of this patent is extended or adjusted under 35 U.S.C. 154(b) by 0 days.

(21) Appl. No.: 18/932,758

(22) Filed: Oct. 31, 2024

Related U.S. Application Data

(63) Continuation of application No. 18/921,362, filed on Oct. 21, 2024.

(51) Int. Cl.
*A61B 5/1172* (2016.01)
*G06V 40/12* (2022.01)

(52) U.S. Cl.
CPC ........ *A61B 5/1172* (2013.01); *G06V 40/1353* (2022.01); *G06V 40/1359* (2022.01)

(58) Field of Classification Search
CPC .............. A61B 5/1172; G06V 40/1353; G06V 40/1359
See application file for complete search history.

(56) References Cited

U.S. PATENT DOCUMENTS

| | | | | |
|---|---|---|---|---|
| 4,896,363 A | * | 1/1990 | Taylor | G07C 9/37 382/125 |
| 6,487,306 B1 | * | 11/2002 | Jain | G06V 40/1347 382/125 |
| 7,142,699 B2 | * | 11/2006 | Reisman | G06V 40/1365 382/209 |
| 7,526,110 B2 | * | 4/2009 | Niinuma | G06F 18/254 382/218 |
| 2004/0125993 A1 | * | 7/2004 | Zhao | G06V 40/12 340/5.53 |
| 2016/0246396 A1 | * | 8/2016 | Dickinson | G06F 3/043 |
| 2020/0127839 A1 | * | 4/2020 | Alzahrani | H04L 9/3231 |
| 2020/0193117 A1 | * | 6/2020 | Raff | G06N 3/048 |

(Continued)

OTHER PUBLICATIONS

Cappelli, Raffaele et al., "Semi-Automatic Enhancement of Very Low Quality Fingerprints," 2009 Proceedings of 6th International Symposium on Image and Signal Processing and Analysis, 2009, pp. 678-683.

(Continued)

*Primary Examiner* — John B Strege
(74) *Attorney, Agent, or Firm* — NIXON & VANDERHYE P.C.

(57) ABSTRACT

A fingerprint recognition system for recognizing fingerprints includes a processor operatively configured for executing digital instructions, and digital storage media operatively connected to the processor and configured for storing instructions configured for directing the processor to carry out the steps of enhancing at least one or more fingerprint images, extracting minutia features from the enhanced fingerprint images, and encoding the fingerprint extracted minutia features as a digital fingerprint.

18 Claims, 13 Drawing Sheets

(56) References Cited

U.S. PATENT DOCUMENTS

2023/0086442 A1* 3/2023 Van Ostrand ....... G06F 3/04166
345/173

OTHER PUBLICATIONS

Chikkerur, Sharat et al., "K-plet and Coupled BFS: A Graph Based Fingerprint Representation and Matching Algorithm," Advances in Biometrics: International Conference, ICB 2006, Hong Kong, China, Jan. 5-7, 2006. Proceedings. Springer (2005), pp. 309-315.
Yoon, Soweon et al., Latent Fingerprint Enhancement via Robust Orientation Field Estimation, 2011 International Joint Conference on Biometrics (IJCB), IEEE (2011), 8 pp.
Feng, Jianjiang et al., Orientation Field Estimation for Latent Fingerprint Enhancement. IEEE Transactions on Pattern Analysis and Machine Intelligence, vol. 35, No. 4, 2012, pp. 925-940.
Yang, Xiao et al., "Localized Dictionaries Based Orientation Field Estimation for Latent Fingerprints," IEEE Transactions on Pattern Analysis and Machine Intelligence, vol. 36, No. 5, 2014, pp. 955-969.
Cao, Kai et al., :Segmentation and Enhancement of Latent Fingerprints: A Coarse to Fine Ridge Structure Dictionary, IEEE Transactions on Pattern Analysis and Machine Intelligence, vol. 36, No. 9, Sep. 2014, pp. 1847-1859.
Wang, Yi et al., "A Fingerprint Orientation Model Bbased on 2d Fourier Expansion (FOMFE) and Its Application to Singular-Point Detection and Fingerprint Indexing," IEEE Transactions on Pattern Analysis and Machine Intelligence, vol. 29, No. 4, Apr. 2007, pp. 573-585.
Maio, D. et al., "FVC2002: Second Fingerprint Verification Competition," 2002 International Conference on Pattern Recognition, vol. 3, 2002, pp. 811-814.
Maltoni, Davide et al., "Handbook of Fingerprint Recognition," Third Edition, vol. 2. Springer, 2009, 111 pp.
Watson, Craig I. et al., "User's Guide to NIST Biometric Image Software (NBIS)," NISTIR 7392, 2007, 207 pp.
Ghafoor, Mubeen et al., "Efficient Fingerprint Matching Using GPU," IET Image Processing, vol. 12, Iss. 2, 2018, pp. 274-284.
Chikkerur, Sharat et al., Fingerprint Image Enhancement Using STFT Analysis, Conference Paper in Lecture Notes in Computer Science, Aug. 2005, 11 pp.
Hawthorne, Mark R. et al., "Fingerprints—Analysis and Understanding the Science," Second Edition, CRC Press, Taylor & Francis Group, 2021, 30 pp.
Hong, Lin et al., "Fingerprint Image Enhancement: Algorithm and Performance Evaluation," IEEE Transactions on Pattern Analysis and Machine Intelligence, vol. 20, No. 8, Aug. 1998, pp. 777-789.
Ratha, Nalini K. et al., "Adaptive Flow Orientation-Based Feature Extraction in Fingerprint Images," Pattern Recognition, vol. 28, No. 11, 1995, pp. 1657-1672.
Sankaran, Anush et al., "Latent Fingerprint Matching: A Survey," IEEE Access, The Journal for Rapid Open Access Publishing, vol. 2, Aug. 20, 2014, pp. 982-1004.
Schuch, Patrick et al., "Survey on the Impact of Fingerprint Image Enhancement," IET Biometrics, vol. 7, Iss. 2, 2018, pp. 102-115.
Yoon, Soweon et al., "On Latent Fingerprint Enhancement," Department of Computer Science and Engineering, Michigan State University and Department of Brain and Cognitive Engineering, Korea University, Publication Date Unknown, 10 pp.
Zhang, Jiangyang et al., "Adaptive Directional Total-Variation Model for Latent Fingerprint Segmentation," IEEE Transactions on Information Forensics and Security, vol. 8, No. 8, Aug. 2013, pp. 1261-1273.

* cited by examiner

FINGERPRINT RECOGNITION SYSTEM AND METHOD THEREFOR

CROSS-REFERENCES TO RELATED APPLICATIONS

This application is a continuation of U.S. patent application Ser. No. 18/921,362, filed Oct. 21, 2024, pending, the entire contents of which are hereby incorporated by reference in this application.

FIELD OF THE INVENTION

The present invention relates to a fingerprint recognition system and method therefor and in particular to a fingerprint recognition system and method for more accurately recognizing latent fingerprints.

The invention has been developed primarily for use in/with fingerprint recognition and will be described hereinafter with reference to this application. However, it will be appreciated that the invention is not limited to this particular field of use.

BACKGROUND OF THE INVENTION

At present fingerprints are widely used for human verification and identification in a range of civil and criminal applications. Unlike plain and professionally acquired rolled fingerprints, latent fingerprints are inadvertent finger skin impressions typically left at criminal events and serve as crucial evidence for identifying perpetrators by law enforcement and forensic organizations. Latent fingerprints typically exhibit smudges, blurred regions, unclear ridge structures, and complex background noise, unlike plain and rolled fingerprints.

Since the identification accuracy of latent fingerprints is heavily dependent on their quality, the accuracy may be significantly lower compared to plain and rolled fingerprints.

For this reason, latent fingerprint enhancement has become a crucial step in preprocessing for accurate identification. Only approaches to fingerprint enhancement relied on conventional image processing techniques, such as contextual and directional filtering. In one instance, a method was proposed by Capelli et al (Cappelli, R., Maio, D., Maltoni, D.: *Semi-automatic enhancement of very low quality fingerprints. In:* 2009 *Proceedings of 6th International Symposium on Image and Signal Processing and Analysis.* pp. 678-683. IEEE (2009)) that adjusts Gabor filters to local fingerprint characteristics in order to reduce noise and enhance ridge clarity. Similarly Chikkerur et al. (Chikkerur, S., Cartwright, A. N., Govindaraju, V.: *K-plet and coupled bfs: a graph based fingerprint representation and matching algorithm. In: Advances in Biometrics: International Conference, ICB* 2006, Hong Kong, China, Jan. 5-7, 2006. *Proceedings*. pp. 309-315. Springer (2005)) introduced contextual filtering in the Fourier domain for the same purpose. However, these methodologies demonstrate superior performance when applied to low quality plain or rolled fingerprints. Challenges arise when attempting to enhance latent fingerprints due to two main factors: 1) structural noise leading to distorted ridge structures in latent fingerprints; and 2) challenges in accurate orientation and frequency estimation due to the unclear ridge structures of latent fingerprints.

Consequently, a variety of global and smoothing modelling techniques have been proposed to tackle these challenges and improve reliable orientation estimation. Yoon et al (Yoon, S., Feng, J., Jain, A. K.: *Latent fingerprint enhancement via robust orientation field estimation. In:* 2011 *international joint conference on biometrics (IJCB)*. pp. 1-8. *IEEE* (2011)) recommended the use of a polynomial model in conjunction with Gabor filters for estimating the orientation of fingerprints. Feng et al (Feng, J., Zhou, J., Jain, A. K.: *Orientation field estimation for latent fingerprint enhancement. IEEE transactions on pattern analysis and machine intelligence* 35(4), 925-940 (2012)) the application of an orientation patch dictionary for orientation estimation, followed by Gabor filtering to improve latent fingerprints. Yang et al (Yang, X., Feng, J., Zhou, J.: *Localized dictionaries based orientation field estimation for latent fingerprints. IEEE transactions on pattern analysis and machine intelligence* 36(5), 955-969 (2014)) further refine this method by substituting the orientation dictionary with localised orientation dictionaries. While Gabor filters excel in enhancing fingerprints, their reliance on a fixed ridge frequency poses a limitation, as fingerprint ridge frequencies naturally vary. To overcome this, researchers have explored techniques based on total variation (TV) image models. These models aim to minimize the overall variation within the image, effectively separating the textured fingerprint ridges from the background, leading to improved fingerprint enhancements. Examples of such research include:

a. Cao et al (Cao, K., Liu, E., Jain, A. K.: *Segmentation and enhancement of latent fingerprints: A coarse to fine ridge structure dictionary. IEEE Transactions on Pattern Analysis and Machine Intelligence* 36(9), 1847-1859 (2014))

b. Wang et al (Wang, Y., Hu, J., Phillips, D.: *A fingerprint orientation model based on 2d fourier expansion (fomfe) and its application to singular-point detection and fingerprint indexing. IEEE Transactions on Pattern Analysis and Machine Intelligence* 29(4), 573-585 (2007))

c. Yang et al (Yang, X., Feng, J., Zhou, J.: *Localized dictionaries based orientation field estimation for latent fingerprints. IEEE transactions on pattern analysis and machine intelligence* 36(5), 955-969 (2014))

Any discussion of the background art throughout the specification should in no way be considered as an admission that such background art is prior art, nor that such background art is widely known or forms part of the common general knowledge in the field in Australia or any other country.

SUMMARY OF THE INVENTION

The invention seeks to provide a fingerprint recognition system and method therefor which will overcome or substantially ameliorate at least some of the deficiencies of the prior art, or to at least provide an alternative.

According to a first aspect, the present invention may be said to involve a fingerprint recognition system for recognizing fingerprints, the fingerprint recognition system including:

a. a processor operatively configured for executing digital instructions;

b. digital storage media operatively connected to the processor and configured for storing instructions configured for directing the processor to carry out the steps of:

i. enhancing the at least one or more fingerprint images;

ii. extracting minutia features from the enhanced fingerprint images; and iii. encoding the fingerprint extracted minutia features as a digital fingerprint.

In one embodiment, the fingerprint recognition system includes a transceiver for transmitting and/or receiving data, and the fingerprint recognition system is configured for:
a. receiving at least one more fingerprint images of a fingerprint.

Fingerprint Enhancement

In one embodiment, the instructions are configured for directing the processor to carry out the step of:
a. selecting a fingerprint region of interest; and
b. enhancing the at least one more fingerprint images by separating the fingerprint region of interest from the background as a separated fingerprint.

In one embodiment, the instructions are configured for directing the processor to carry out the step of:
a. separating the fingerprint region of interest from the background by using the average magnitude of the gradient.

In one embodiment, the instructions are configured for directing the processor to carry out the step of:
a. calculating local ridge orientations and frequencies of the separated fingerprint.

In one embodiment, the instructions are configured for directing the processor to carry out the step of:
a. calculating ridge orientations using the inverse tangent of the gradient in both horizontal and vertical directions to generate an orientation image.

In one embodiment, the orientation image contains the local ridge angles at each point of the separated fingerprint.

In one embodiment, the instructions are configured for directing the processor to carry out the step of:
a. estimating ridge frequencies by dividing the separated region of interest into blocks.

In one embodiment, the instructions are configured for directing the processor to carry out the step of:
a. rotating each block to align the ridges vertically In one embodiment, the instructions are configured for directing the processor to carry out the step of:
a. dividing each rotated block into equal segments; and
b. calculating the vertical projection of each segment.

In one embodiment, the instructions are configured for directing the processor to carry out the step of:
a. determining the frequency of each segment by
i. counting the number of peaks; and
ii. dividing by the distance between the first and last peak.

In one embodiment, the instructions are configured for directing the processor to carry out the step of:
a. calculating the dominant frequency of each block using alpha trimmed mean filtering using the segment frequencies.

In one embodiment, the instructions are configured for directing the processor to carry out the step of:
a. enhancing the separated fingerprint using Gabor filters to generate an enhanced image.

In one embodiment, the instructions are configured for directing the processor to carry out the step of:
a. convolving each pixel of the separated fingerprint with a Gabor filter tuned to the calculated local ridge orientations and frequencies.

In one embodiment, the instructions are configured for directing the processor to carry out the step of:
a. generate a set of Gabor filters for the calculated range of frequencies and orientations present in the separated fingerprint.

In one embodiment, the instructions are configured for directing the processor to carry out the step of:
a. enhancing each pixel in the separated fingerprint using a Gabor filter, wherein the frequency and orientation of the Gabor filter are closest to the frequency and orientation of the pixel.

In one embodiment, the instructions are configured for directing the processor to carry out the step of:
a. enhancing each pixel in the separated fingerprint using a Gabor filter, wherein the Gabor filter is described by $$g(x, y : \theta_p, f_p) = \exp\left[-\frac{1}{2}\left(\frac{x_{\theta_p}^2}{\sigma_x^2} + \frac{y_{\theta_p}^2}{\sigma_y^2}\right)\right]\cos(2\pi f_p x_{\theta_p})$$

where $x_{\theta_p} = x \cos(\theta_p) + y \sin(\theta_p)$ $y_{\theta_p} = x \sin(\theta_p) + y \cos(\theta_p)$ and $\theta_p$ is the pixel's orientation;
$f_p$ is the pixel's frequency; and
$\sigma_x$ and $\sigma_y$ are the standard deviations of the Gaussian envelope along the
x and y axes, respectively.

In one embodiment, the instructions are configured for directing the processor to carry out the step of:
a. converting the enhanced image into a ridge/valley skeleton to facilitate the extraction of minutia features.

In one embodiment, the instructions are configured for directing the processor to carry out the step of:
a. converting the enhanced image into a binary image by classifying all pixels in the enhanced image as either once or zeros based on a selected threshold.

In one embodiment, the instructions are configured for directing the processor to carry out the step of:
a. thinning the binary image to reduce the ridge width to a single pixel.

Feature Extraction

In one embodiment, the instructions are configured for directing the processor to carry out the step of:
a. scanning the local region of each pixel.

In one embodiment, the instructions are configured for directing the processor to carry out the step of:
a. scanning the local region of each pixel including each adjacent pixel.

In one embodiment, the instructions are configured for directing the processor to carry out the step of:
a. scanning the local region of each pixel including each adjacent pixel in a 3×3 window.

In one embodiment, the instructions are configured for directing the processor to carry out the step of:
a. classifying the ridge pixel as a minutia based on the number of transitions from 0 to 1 that occurred during the scanning of the adjacent pixels.

In one embodiment, the instructions are configured for directing the processor to carry out the step of:
a. classifying the ridge pixel as a minutia based on the number of transitions from 0 to 1 that occurred during the scanning of the adjacent pixels in a clockwise direction.

In one embodiment, the instructions are configured for directing the processor to carry out the step of:
   a. removing false minutia.

Feature Encoding

In one embodiment, the instructions are configured for directing the processor to carry out the step of:
   a. encoding each minutia point based on its adjacent minutia, with the minutia point being the reference.

In one embodiment, the instructions are configured for directing the processor to carry out the step of:
   a. creating a list of n neighboring minutia points to a reference minutia, excluding the reference minutia itself, based on the Euclidean distance between the reference minutia and a minutia list.

In one embodiment, the instructions are configured for directing the processor to carry out the step of:
   a. based on the Euclidean distance between minutia ($M_i$) and all other minutiae in minutiae list ($M_L$), create a new list ($M_i^{Nearest}$) of n nearest neighboring minutiae points, excluding the reference minutia ($M_i$) itself.

In one embodiment, the new list ($M_i^{Nearest}$) can be expressed as $$M_i^{Nearest}(x_k, y_k, \theta_k) = M_L(x_j, y_j, \theta_j)$$

Where k=1:n iterates through the indices of the nearest minutia points, and j represents the index of each nearest minutia point from minutiae list ($M_L$).

In one embodiment, the instructions are configured for directing the processor to carry out the step of:
   a. generating an encoded list of minutia using the relative distance and angle between the reference minutia and the neighboring minutiae.

In one embodiment, the instructions are configured for directing the processor to carry out the step of:
   a. generating an encoded list of minutia by considering the relative distance and angle features between a focal minutia and its neighboring minutiae, wherein the features ($\rho_j$, $\theta_j$, $\phi_j$) are computed by the following equations:

$$\rho_j = \sqrt{dx_j^2 + dy_j^2}$$
$$\theta_j = \tan^{-1}\left(\frac{dy_j}{dx_j}\right)$$
where,
$$\phi_j = M_L(3 \times (i-1) + 2) - M_i^{Nearest}(3 \times (j-1) + 2)$$
$$dx_j = M_L(3 \times (i-1)) - M_i^{Nearest}(3 \times (j-1))$$
$$dy_j = M_L(3 \times (i-1) + 1) - M_i^{Nearest}(3 \times (j-1) + 1)$$

In one embodiment, the instructions are configured for directing the processor to carry out the step of:
   a. generating a final encoded minutia list for a given fingerprint comprising a combination of all individual minutia encodings.

In one embodiment, the instructions are configured for directing the processor to carry out the step of:
   a. storing the encoded minutia list as a finger code.

In one embodiment, the instructions are configured for directing the processor to carry out the step of:
   a. storing a plurality of finger codes in a database as a candidate database.

Feature Matching

In one embodiment, the instructions are configured for directing the processor to carry out the step of:
   a. receiving an image of a template fingerprint as a template image;
   b. enhancing the at least one or more template images;
   c. extracting minutia features from the enhanced template images; and
   d. encoding the fingerprint extracted minutia features as a template finger code.

In one embodiment, the instructions are configured for directing the processor to carry out the step of:
   a. comparing the template finger code to at least one or more of the stored finger codes in the candidate database.

In one embodiment, the instructions are configured for directing the processor to carry out the step of:
   a. comparing the template finger code to at least one or more of the stored finger codes in the candidate database to determine a similarity score.

In one embodiment, the instructions are configured for directing the processor to carry out the step of:
   a. comparing the template finger code to at least one or more of the stored finger codes in the candidate database using an exhaustive point pattern search algorithm.

In one embodiment, the instructions are configured for directing the processor to carry out the step of:
   a. matching each minutia from the template finger code with every minutia in the candidate finger code.

In one embodiment, the instructions are configured for directing the processor to carry out the step of:
   a. calculating a similarity score from the matching of the each minutia from the template finger code with every minutia in the candidate finger code.

In one embodiment, the instructions are configured for directing the processor to carry out the step of:
   a. matching a minutia pair of candidate minutia from the candidate finger code and template minutia from the template finger code by comparing the encoded features.

In one embodiment, the instructions are configured for directing the processor to carry out the step of:
   a. determining the result of the comparison of the encoded features ($\rho i$, $\theta i$, $\phi i$) of the candidate minutia and the encoded features ($\rho j$, $\theta j$, $\phi j$) of the template minutia according to the following algorithm $$Acc_{i,j} = \begin{cases} 1, & \text{if } \left(\sum_{k=1}^{n^2} D_{i,j}(k)\right) \geq T_N \\ 0, & \text{otherwise} \end{cases}$$

$$D_{i,j}(k) = \begin{cases} 1, & \text{if } (T_\rho(i,j) \wedge T_\theta(i,j) \wedge T_\phi(i,j)) \\ 0, & \text{otherwise} \end{cases}$$

where
$$T_\rho(i,j) = \Delta\rho_{i,j}(k) \leq T_\rho$$
$$T_\theta(i,j) = \{(\Delta\theta_{i,j}(k) \leq T_\theta) \vee (\Delta\theta_{i,j}(k) \geq 180 - T_\theta)\}$$
$$T_\phi(i,j) = \{(\Delta\phi_{i,j}(k) \leq T_\phi) \vee (\Delta\phi_{i,j}(k) \geq 180 - T_\phi)\}$$

and where ($T\rho$, $T\theta$, and $T\phi$) are distinct thresholds for features ($\rho i$, $\theta i$, and $\phi i$);
and wherein $\Delta\rho i,j(k)$, $\Delta\theta i,j(k)$, and $\Delta\phi i,j(k)$ are calculated as indicated in the following equations:

$$\Delta\rho_{i,j}(k) = F^T\left(3 \times \text{floor}\left(\frac{k-1}{n}\right)\right) - F^C(3 \times \text{mod}(n(k-1)))$$

$$\Delta\theta_{i,j}(k) = F^T\left(3 \times \text{floor}\left(\frac{k-1}{n}\right) + 1\right) - F^C(3 \times \text{mod}(n(k-1)) + 1)$$

$$\Delta\phi_{i,j}(k) = F^T\left(3 \times \text{floor}\left(\frac{k-1}{n}\right) + 2\right) - F^C(3 \times \text{mod}(n(k-1)) + 2)$$

In one embodiment, the instructions are configured for directing the processor to carry out the step of:
a. calculating a similarity score by calculating a matrix that acts as an accumulator for every minutia pair.

In one embodiment, the instructions are configured for directing the processor to carry out the step of:
a. calculating a matrix according to the following algorithm $$\text{Sim} = 100 \times \left( \frac{M_{mat}^{pair}}{\min(M, N)} \right)$$

where
Sim is the similarity score
$M_{ssat}^{pair}$ is the matched minutia pair,
M and N are the number of minutia of the of the candidate finger code and the template finger code $$M_{mat}^{pair} = \sum_{i=1}^{N} \sum_{j=1}^{M} (S_{matrix}(N \times (i-1) + (j-1)))$$

$$S_{Matrix}(N \times (i-1) + (j-1)) = Acc_{i,j}$$

According to a further aspect, the present invention may be said to involve a method of recognizing fingerprints, the method being carried out on an electronic device and including:
a. receiving at least one more fingerprint images of a fingerprint;
b. enhancing the at least one or more fingerprint images;
c. extracting minutia features from the enhanced fingerprint images; and
d. encoding the fingerprint extracted minutia features as a digital fingerprint.

In one embodiment, the method includes the step of
a. receiving at least one more fingerprint images of a fingerprint.

Fingerprint Enhancement

In one embodiment, the method includes:
a. selecting a fingerprint region of interest; and
b. enhancing the at least one more fingerprint images by separating the fingerprint region of interest from the background as a separated fingerprint.

In one embodiment, the method includes:
a. separating the fingerprint region of interest from the background by using the average magnitude of the gradient.

In one embodiment, the method includes:
a. calculating local ridge orientations and frequencies of the separated fingerprint.

In one embodiment, the method includes:
a. calculating ridge orientations using the inverse tangent of the gradient in both horizontal and vertical directions to generate an orientation image.

In one embodiment, the orientation image contains the local ridge angles at each point of the separated fingerprint.

In one embodiment, the method includes:
a. estimating ridge frequencies by dividing the separated region of interest into blocks.

In one embodiment, the method includes:
a. rotating each block to align the ridges vertically In one embodiment, the method includes:
a. dividing each rotated block into equal segments; and
b. calculating the vertical projection of each segment.

In one embodiment, the method includes:
a. determining the frequency of each segment by
  i. counting the number of peaks; and
  ii. dividing by the distance between the first and last peak.

In one embodiment, the method includes:
a. calculating the dominant frequency of each block using alpha trimmed mean filtering using the segment frequencies.

In one embodiment, the method includes:
a. enhancing the separated fingerprint using Gabor filters to generate an enhanced image.

In one embodiment, the method includes:
a. convolving each pixel of the separated fingerprint with a Gabor filter tuned to the calculated local ridge orientations and frequencies.

In one embodiment, the method includes:
a. generate a set of Gabor filters for the calculated range of frequencies and orientations present in the separated fingerprint.

In one embodiment, the method includes:
a. enhancing each pixel in the separated fingerprint using a Gabor filter, wherein the frequency and orientation of the Gabor filter are closest to the frequency and orientation of the pixel.

In one embodiment, the method includes:
a. enhancing each pixel in the separated fingerprint using a Gabor filter, wherein the Gabor filter is described by $$g(x, y: \theta_p, f_p) = \exp\left[-\frac{1}{2}\left(\frac{x_{\theta_p}^2}{\sigma_x^2} + \frac{y_{\theta_p}^2}{\sigma_y^2}\right)\right] \cos(2\pi f_p x_{\theta_p})$$

where
$x_{\theta_p} = x\cos(\theta_p) + y\sin(\theta_p)$
$y_{\theta_p} = -x\sin(\theta_p) + y\cos(\theta_p)$ and
$\theta_p$ is the pixel's orientation;
$f_p$ is the pixel's frequency; and
$\sigma_x$ and $\sigma_y$ are the standard deviations of the Gaussian envelope along the
x and y axes, respectively.

In one embodiment, the method includes:
a. converting the enhanced image into a ridge/valley skeleton to facilitate the extraction of minutia features.

In one embodiment, the method includes:
a. converting the enhanced image into a binary image by classifying all pixels in the enhanced image as either once or zeros based on a selected threshold.

In one embodiment, the method includes:
a. thinning the binary image to reduce the ridge width to a single pixel.

Feature Extraction

In one embodiment, the method includes:
a. scanning the local region of each pixel.

In one embodiment, the method includes:
a. scanning the local region of each pixel including each adjacent pixel.

In one embodiment, the method includes:
a. scanning the local region of each pixel including each adjacent pixel in a 3×3 window.

In one embodiment, the method includes:
a. classifying the ridge pixel as a minutia based on the number of transitions from 0 to 1 that occurred during the scanning of the adjacent pixels.

In one embodiment, the method includes:
a. classifying the ridge pixel as a minutia based on the number of transitions from 0 to 1 that occurred during the scanning of the adjacent pixels in a clockwise direction.

In one embodiment, the method includes:
a. removing false minutia.

Feature Encoding

In one embodiment, the method includes:
a. encoding each minutia point based on its adjacent minutia, with the minutia point being the reference.

In one embodiment, the method includes:
a. creating a list of n neighboring minutia points to a reference minutia, excluding the reference minutia itself, based on the Euclidean distance between the reference minutia and a minutia list.

In one embodiment, the method includes:
a. based on the Euclidean distance between minutia ($M_i$) and all other minutiae in minutiae list ($M_L$), create a new list ($M_i^{Nearest}$) of n nearest neighboring minutiae points, excluding the reference minutia ($M_i$) itself.

In one embodiment, the new list ($M_i^{Nearest}$) can be expressed as $$M_i^{Nearest}(x_k, y_k, \theta_k) = M_L(x_j, y_j, \theta_j)$$

Where k=1:n iterates through the indices of the nearest minutia points, and j represents the index of each nearest minutia point from minutiae list ($M_L$).

In one embodiment, the method includes:
a. generating an encoded list of minutia using the relative distance and angle between the reference minutia and the neighbouring minutiae.

In one embodiment, the method includes:
a. generating an encoded list of minutia by considering the relative distance and angle features between a focal minutia and its neighbouring minutiae, wherein the features ($\rho_j$, $\theta_j$, $\phi_j$) are computed by the following equations:

$$\rho_j = \sqrt{dx_j^2 + dy_j^2}$$

$$\theta_j = \tan^{-1}\left(\frac{dy_j}{dx_j}\right)$$

where,
$$\phi_j = M_L(3 \times (i-1) + 2) - M_i^{Nearest}(3 \times (j-1) + 2)$$
$$dx_j = M_L(3 \times (i-1)) - M_i^{Nearest}(3 \times (j-1))$$
$$dy_j = M_L(3 \times (i-1) + 1) - M_i^{Nearest}(3 \times (j-1) + 1)$$

In one embodiment, the method includes:
a. generating a final encoded minutia list for a given fingerprint comprising a combination of all individual minutia encodings.

In one embodiment, the method includes:
a. storing the encoded minutia list as a finger code.

In one embodiment, the method includes:
a. storing a plurality of finger codes in a database as a candidate database.

Feature Matching

In one embodiment, the method includes:
a. receiving an image of a template fingerprint as a template image;
b. enhancing the at least one or more template images;
c. extracting minutia features from the enhanced template images; and
d. encoding the fingerprint extracted minutia features as a template finger code.

In one embodiment, the method includes:
a. comparing the template finger code to at least one or more of the stored finger codes in the candidate database.

In one embodiment, the method includes:
a. comparing the template finger code to at least one or more of the stored finger codes in the candidate database to determine a similarity score.

In one embodiment, the method includes:
a. comparing the template finger code to at least one or more of the stored finger codes in the candidate database using an exhaustive point pattern search algorithm.

In one embodiment, the method includes:
a. matching each minutia from the template finger code with every minutia in the candidate finger code.

In one embodiment, the method includes:
a. calculating a similarity score from the matching of the each minutia from the template finger code with every minutia in the candidate finger code.

In one embodiment, the method includes:
a. matching a minutia pair of candidate minutia from the candidate finger code and template minutia from the template finger code by comparing the encoded features.

In one embodiment, the method includes:
a. determining the result of the comparison of the encoded features ($\rho i$, $\theta i$, $\phi i$) of the candidate minutia and the encoded features ($\rho j$, $\theta j$, $\phi j$) of the template minutia according to the following algorithm $$Acc_{i,j} = \begin{cases} 1, & \text{if } \left(\sum_{k=1}^{n^2} D_{i,j}(k)\right) \geq T_N \\ 0, & \text{otherwise} \end{cases}$$

$$D_{i,j}(k) = \begin{cases} 1, & \text{if } (T_\rho(i,j) \wedge T_\theta(i,j) \wedge T_\phi(i,j)) \\ 0, & \text{otherwise} \end{cases}$$

where
$T_\rho(i,j) = \Delta\rho_{i,j}(k) \leq T_\rho$
$T_\theta(i,j) = \{(\Delta\theta_{i,j}(k) \leq T_\theta) \vee (\Delta\theta_{i,j}(k) \geq 180 - T_\theta)\}$
$T_\phi(i,j) = \{(\Delta\phi_{i,j}(k) \leq T_\phi) \vee (\Delta\phi_{i,j}(k) \geq 180 - T_\phi)\}$ and where ($T\rho$, $T\theta$, and $T\phi$) are distinct thresholds for features ($\rho i$, $\theta i$, and $\phi i$);
and wherein $\Delta\rho i,j(k)$, $\Delta\theta i,j(k)$, and $\Delta\phi i,j(k)$ are calculated as indicated in the following equations:

$$\Delta\rho_{i,j}(k) = F^T\left(3 \times \text{floor}\left(\frac{k-1}{n}\right)\right) - F^C(3 \times \text{mod}(n(k-1)))$$

$$\Delta\theta_{i,j}(k) = F^T\left(3 \times \text{floor}\left(\frac{k-1}{n}\right) + 1\right) - F^C(3 \times \text{mod}(n(k-1)) + 1)$$

$$\Delta\phi_{i,j}(k) = F^T\left(3 \times \text{floor}\left(\frac{k-1}{n}\right) + 2\right) - F^C(3 \times \text{mod}(n(k-1)) + 2)$$

In one embodiment, the method includes:
a. calculating a similarity score by calculating a matrix that acts as an accumulator for every minutia pair.

In one embodiment, the method includes:
a. calculating a matrix according to the following algorithm $$\text{Sim} = 100 \times \left(\frac{M_{mat}^{pair}}{\min(M, N)}\right)$$

where
Sim is the similarity score
$M_{ssat}^{pair}$ is the matched minutia pair, M and N are the number of minutia of the of the candidate finger code and the template finger code $$M_{mat}^{pair} = \sum_{i=1}^{N}\sum_{j=1}^{M}(S_{Matrix}(N\times(i-1)+(j-1)))$$

$$S_{Matrix}(N\times(i-1)+(j-1)) = Acc_{i,j}$$

According to a further aspect, the present invention may be said to involve a fingerprint recognition system for recognizing fingerprints, the fingerprint recognition system including:
 a. a fingerprint image enhancement module configured for enhancing at least one or more fingerprint images;
 b. a minutiae extraction module configured for extracting minutia features from the enhanced fingerprint images; and
 c. an encoding module configured for encoding the fingerprint extracted minutia features as a digital finger code.

In one embodiment, the fingerprint recognition system includes a transceiver module configured for at least receiving at least one or more fingerprint images of a fingerprint.

Fingerprint Enhancement

In one embodiment, the fingerprint image enhancement module is configured for directing the processor to carry out the step of:
 a. selecting a fingerprint region of interest; and
 b. enhancing the at least one more fingerprint images by separating the fingerprint region of interest from the background as a separated fingerprint.

In one embodiment, the fingerprint image enhancement module is configured for directing the processor to carry out the step of:
 a. separating the fingerprint region of interest from the background by using the average magnitude of the gradient.

In one embodiment, the fingerprint image enhancement module is configured for directing the processor to carry out the step of:
 a. calculating local ridge orientations and frequencies of the separated fingerprint.

In one embodiment, the fingerprint image enhancement module is configured for directing the processor to carry out the step of:
 a. calculating ridge orientations using the inverse tangent of the gradient in both horizontal and vertical directions to generate an orientation image.

In one embodiment, the orientation image contains the local ridge angles at each point of the separated fingerprint.

In one embodiment, the fingerprint image enhancement module is configured for directing the processor to carry out the step of:
 a. estimating ridge frequencies by dividing the separated region of interest into blocks.

In one embodiment, the fingerprint image enhancement module is configured for directing the processor to carry out the step of:
 a. rotating each block to align the ridges vertically In one embodiment, the fingerprint image enhancement module is configured for directing the processor to carry out the step of:
 a. dividing each rotated block into equal segments; and
 b. calculating the vertical projection of each segment.

In one embodiment, the fingerprint image enhancement module is configured for directing the processor to carry out the step of:
 a. determining the frequency of each segment by
  i. counting the number of peaks; and
  ii. dividing by the distance between the first and last peak.

In one embodiment, the fingerprint image enhancement module is configured for directing the processor to carry out the step of:
 a. calculating the dominant frequency of each block using alpha trimmed mean filtering using the segment frequencies.

In one embodiment, the fingerprint image enhancement module is configured for directing the processor to carry out the step of:
 a. enhancing the separated fingerprint using Gabor filters to generate an enhanced image.

In one embodiment, the fingerprint image enhancement module is configured for directing the processor to carry out the step of:
 a. convolving each pixel of the separated fingerprint with a Gabor filter tuned to the calculated local ridge orientations and frequencies.

In one embodiment, the fingerprint image enhancement module is configured for directing the processor to carry out the step of:
 a. generate a set of Gabor filters for the calculated range of frequencies and orientations present in the separated fingerprint.

In one embodiment, the fingerprint image enhancement module is configured for directing the processor to carry out the step of:
 a. enhancing each pixel in the separated fingerprint using a Gabor filter, wherein the frequency and orientation of the Gabor filter are closest to the frequency and orientation of the pixel.

In one embodiment, the fingerprint image enhancement module is configured for directing the processor to carry out the step of:
 a. enhancing each pixel in the separated fingerprint using a Gabor filter, wherein the Gabor filter is described by $$g(x, y: \theta_p, f_p) = \exp\left[-\frac{1}{2}\left(\frac{x_{\theta_p}^2}{\sigma_x^2} + \frac{y_{\theta_p}^2}{\sigma_y^2}\right)\right]\cos(2\pi f_p x_{\theta_p})$$

where $$x_{\theta_p} = x\cos(\theta_p) + y\sin(\theta_p)$$

$$y_{\theta_p} = -x\sin(\theta_p) + y\cos(\theta_p)$$

and
 $\theta_p$ is the pixel's orientation;
 $f_p$ is the pixel's frequency; and
 $\sigma_x$ and $\sigma_y$ are the standard deviations of the Gaussian envelope along the x and y axes, respectively.

In one embodiment, the fingerprint image enhancement module is configured for directing the processor to carry out the step of:
 a. converting the enhanced image into a ridge/valley skeleton to facilitate the extraction of minutia features.

In one embodiment, the fingerprint image enhancement module is configured for directing the processor to carry out the step of:

a. converting the enhanced image into a binary image by classifying all pixels in the enhanced image as either once or zeros based on a selected threshold.

In one embodiment, the fingerprint image enhancement module is configured for directing the processor to carry out the step of:

a. thinning the binary image to reduce the ridge width to a single pixel.

Feature Extraction

In one embodiment, the minutiae extraction module is configured for directing the processor to carry out the step of:

a. scanning the local region of each pixel.

In one embodiment, the minutiae extraction module is configured for directing the processor to carry out the step of:

a. scanning the local region of each pixel including each adjacent pixel.

In one embodiment, the minutiae extraction module is configured for directing the processor to carry out the step of:

a. scanning the local region of each pixel including each adjacent pixel in a 3×3 window.

In one embodiment, the minutiae extraction module is configured for directing the processor to carry out the step of:

a. classifying the ridge pixel as a minutia based on the number of transitions from 0 to 1 that occurred during the scanning of the adjacent pixels.

In one embodiment, the minutiae extraction module is configured for directing the processor to carry out the step of:

a. classifying the ridge pixel as a minutia based on the number of transitions from 0 to 1 that occurred during the scanning of the adjacent pixels in a clockwise direction.

In one embodiment, the minutiae extraction module is configured for directing the processor to carry out the step of:

a. removing false minutia.

Feature Encoding

In one embodiment, the encoding module is configured for directing the processor to carry out the step of:

a. encoding each minutia point based on its adjacent minutia, with the minutia point being the reference.

In one embodiment, the encoding module is configured for directing the processor to carry out the step of:

a. creating a list of n neighboring minutia points to a reference minutia, excluding the reference minutia itself, based on the Euclidean distance between the reference minutia and a minutia list.

In one embodiment, the encoding module is configured for directing the processor to carry out the step of:

a. based on the Euclidean distance between minutia ($M_i$) and all other minutiae in minutiae list ($M_L$), create a new list ($M_i^{Nearest}$) of n nearest neighboring minutiae points, excluding the reference minutia ($M_i$) itself.

In one embodiment, the new list ($M_i^{Nearest}$) can be expressed as $M_i^{Nearest}(x_k, y_k, \theta_k) = M_L(x_j, y_j, \theta_j)$ Where k=1:n iterates through the indices of the nearest minutia points, and j represents the index of each nearest minutia point from minutiae list ($M_L$).

In one embodiment, the encoding module is configured for directing the processor to carry out the step of:

a. generating an encoded list of minutia using the relative distance and angle between the reference minutia and the neighbouring minutiae.

In one embodiment, the encoding module is configured for directing the processor to carry out the step of:

a. generating an encoded list of minutia by considering the relative distance and angle features between a focal minutia and its neighbouring minutiae, wherein the features ($\rho_j$, $\theta_j$, $\phi_j$) are computed by the following equations:

$$\rho_j = \sqrt{dx_j^2 + dy_j^2}$$

$$\theta_j = \tan^{-1}\left(\frac{dy_j}{dxx_j}\right)$$

$$\phi_j = M_L(3 \times (i-1) + 2) - M_i^{Nearest}(3 \times (j-1) + 2)$$

where, $$dx_j = M_L(3 \times (i-1)) - M_i^{Nearest}(3 \times (j-1))$$

$$dy_j = M_L(3 \times (i-1) + 1) - M_i^{Nearest}(3 \times (j-1) + 1)$$

In one embodiment, the encoding module is configured for directing the processor to carry out the step of:

a. generating a final encoded minutia list for a given fingerprint comprising a combination of all individual minutia encodings.

In one embodiment, the encoding module is configured for directing the processor to carry out the step of:

a. storing the encoded minutia list as a finger code.

In one embodiment, the encoding module is configured for directing the processor to carry out the step of:

a. storing a plurality of finger codes in a database as a candidate database.

Feature Matching

In one embodiment, the fingerprint recognition system includes a matching module for matching fingerprints.

In one embodiment, the matching module is configured for directing the processor to carry out the step of:

a. receiving an image of a template fingerprint as a template image;
b. enhancing the at least one or more template images;
c. extracting minutia features from the enhanced template images; and
d. encoding the fingerprint extracted minutia features as a template finger code.

In one embodiment, the matching module is configured for directing the processor to carry out the step of:

a. comparing the template finger code to at least one or more of the stored finger codes in the candidate database.

In one embodiment, the matching module is configured for directing the processor to carry out the step of:

a. comparing the template finger code to at least one or more of the stored finger codes in the candidate database to determine a similarity score.

In one embodiment, the matching module is configured for directing the processor to carry out the step of:

a. comparing the template finger code to at least one or more of the stored finger codes in the candidate database using an exhaustive point pattern search algorithm.

In one embodiment, the matching module is configured for directing the processor to carry out the step of:
  a. matching each minutia from the template finger code with every minutia in the candidate finger code.

In one embodiment, the matching module is configured for directing the processor to carry out the step of:
  a. calculating a similarity score from the matching of the each minutia from the template finger code with every minutia in the candidate finger code.

In one embodiment, the matching module is configured for directing the processor to carry out the step of:
  a. matching a minutia pair of candidate minutia from the candidate finger code and template minutia from the template finger code by comparing the encoded features.

In one embodiment, the matching module is configured for directing the processor to carry out the step of:
  a. determining the result of the comparison of the encoded features ($\rho i$, $\theta i$, $\phi i$) of the candidate minutia and the encoded features ($\rho j$, $\theta j$, $\phi j$) of the template minutia according to the following algorithm $$Acc_{i,j} = \begin{cases} 1, & \text{if } \left(\sum_{k=1}^{a^2} D_{i,j}(k)\right) \geq T_N \\ 0, & \text{otherwise} \end{cases}$$

where $$D_{i,j}(k) = \begin{cases} 1, & \text{if } (T_\rho(i,j) \wedge T_\theta(i,j) \wedge T_\phi(i,j)) \\ 0, & \text{otherwise} \end{cases}$$

$$T_\rho(i,j) = \Delta\rho_{i,j}(k) \leq T_\rho$$

$$T_\theta(i,j) = \{(\Delta\theta_{i,j}(k) \leq T_\theta) \vee (\Delta\theta_{i,j}(k) \geq 180 - T_\theta)\}$$

$$T_\phi(i,j) = \{(\Delta\phi_{i,j}(k) \leq T_\theta) \vee (\Delta\phi_{i,j}(k) \geq 180 - T_\phi)\}$$

and where ($T\rho$, $T\theta$, and $T\phi$) are distinct thresholds for features ($\rho i$, $\theta i$, and $\phi i$);
and wherein $\Delta\rho i,j(k)$, $\Delta\theta i,j(k)$, and $\Delta\phi i,j(k)$ are calculated as indicated in the following equations:

$$\Delta\rho_{i,j}(k) = F^T\left(3 \times \text{floor}\left(\frac{k-1}{n}\right)\right) - F^C(3 \times \text{mod}(n(k-1)))$$

$$\Delta\theta_{i,j}(k) = F^T\left(3 \times \text{floor}\left(\frac{k-1}{n}\right) + 1\right) - F^C(3 \times \text{mod}(n(k-1)) + 1)$$

$$\Delta\phi_{i,j}(k) = F^T\left(3 \times \text{floor}\left(\frac{k-1}{n}\right) + 2\right) - F^C(3 \times \text{mod}(n(k-1)) + 2)$$

In one embodiment, the matching module is configured for directing the processor to carry out the step of:
  a. calculating a similarity score by calculating a matrix that acts as an accumulator for every minutia pair.

In one embodiment, the matching module is configured for directing the processor to carry out the step of:
  a. calculating a matrix according to the following algorithm $$\text{Sim} = 100 \times \left(\frac{M_{mat}^{pair}}{\min(M, N)}\right)$$

where
Sim is the similarity score
$M_{ssat}^{pair}$ is the matched minutia pair,
M and N are the number of minutiae of the candidate finger code and the template finger code $$M_{mat}^{pair} = \sum_{i=1}^{N}\sum_{j=1}^{M}(S_{Matrix}(N \times (i-1) + (j-1)))$$

$$S_{Matrix}(N \times (i-1) + (j-1)) = Acc_{i,j}$$

It should be noted that web servers, client computing device and computer readable storage medium provide the same or similar advantages as the advantages provided by the corresponding computer implemented method, some of which are described herein. Additionally the web server and/or client computing device provides the advantage of deployment across a computer network, such as the Internet, providing distribution, access and economy of scale advantages. Furthermore, the computer readable storage medium provides further advantages, such allowing the deployment of computer instructions for installation and execution by one or more computing devices. Other aspects of the invention are also disclosed.

BRIEF DESCRIPTION OF THE DRAWINGS

Notwithstanding any other forms which may fall within the scope of the present invention, a preferred embodiment of the invention will now be described, by way of example only, with reference to the accompanying drawings in which.

DESCRIPTION OF EMBODIMENTS

Figure 1:
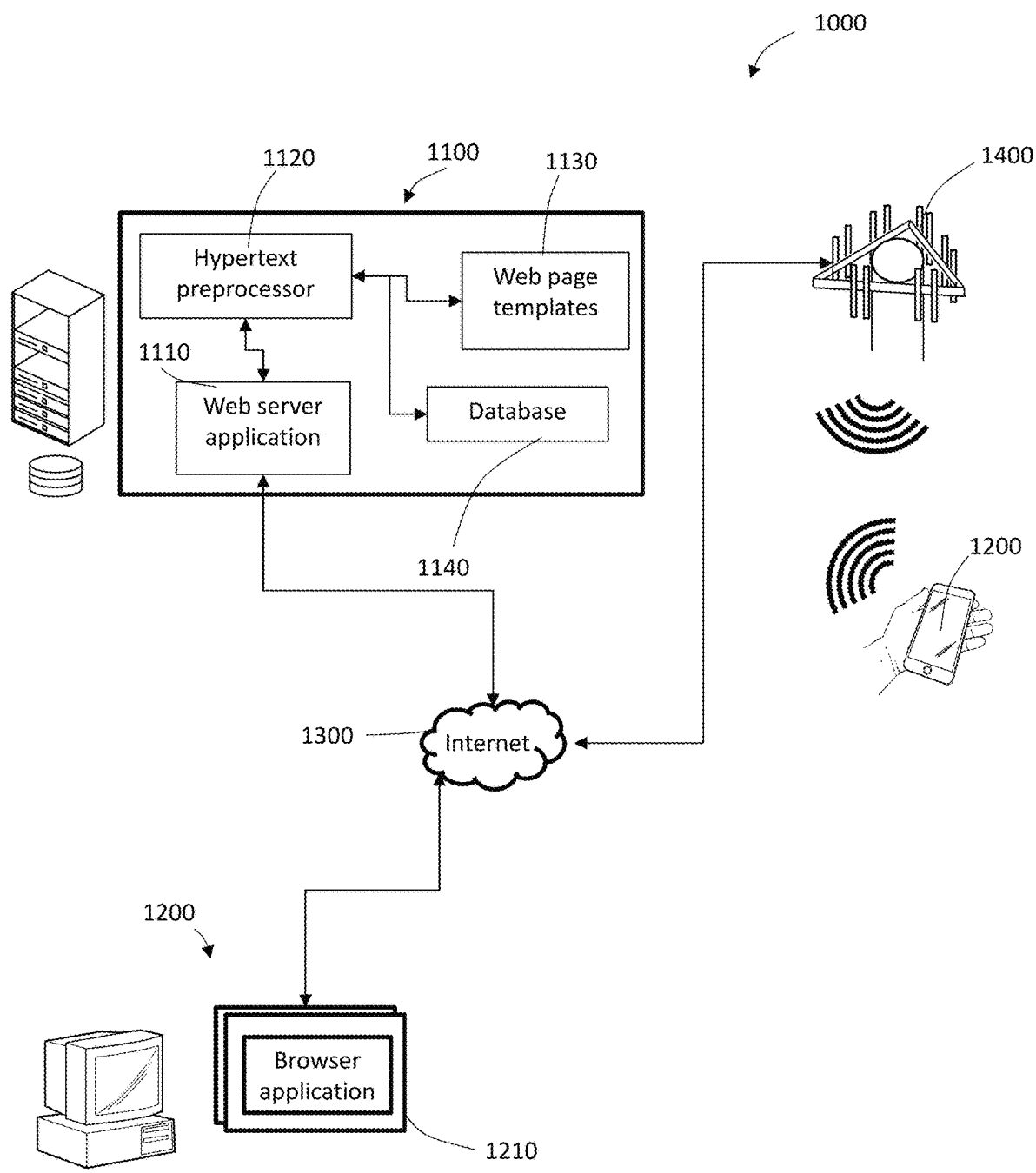
FIG. 1 shows a network of computing devices on which the various embodiments described herein may be implemented in accordance with an embodiment of the present invention.

It should be noted in the following description that like or the same reference numerals in different embodiments denote the same or similar features.

System of Computing Devices

FIG. 1 shows a system 1000 of computing devices adapted for use as a fingerprint recognition system and method therefor, and on which the methods described below may be carried out.

As such, the system 1000 includes a server 1100 for serving web pages to one or more client computing devices 1200 over the Internet 1300.

In a preferred embodiment, the server 1100 is a web server having a web server application 1110 for receiving requests, such as Hypertext Transfer Protocol (HTTP) and File Transfer Protocol (FTP) requests, and serving hypertext web pages or files in response. The web server application 1110 may be, for example the Apache™ or the Microsoft™ IIS HTTP server.

The server 1100 is also provided with a hypertext preprocessor 1120 for processing one or more web page templates 1130 and data from one or more databases 1140 to generate hypertext web pages. The hypertext preprocessor may, for example, be the PHP: Hypertext Preprocessor (PHP) or Microsoft Asp™ hypertext preprocessor. The web server 1100 is also provided with web page templates 1130, such as one or more PHP or ASP files.

Upon receiving a request from the web server application 1110, the hypertext preprocessor 1120 is operable to retrieve a web page template from the web page templates 1130, execute any dynamic content therein, including updating or loading information from the one or more databases 1140, to compose a hypertext web page. The composed hypertext web page may comprise client-side code, such as Javascript, for Document Object Model (DOM) manipulating, asynchronous HTTP requests and the like.

The database 1140 is adapted for storing user account data representing one or more user accounts for users. Such user account data is created by the server 1100 during a user registration process. In this manner, the server 1100 is adapted to update the user account data in relation to the appropriate user account.

Client computing devices 1200 are preferably provided with a browser application 1210, such as the Google Chrome™, Mozilla Firefox™ or Microsoft Internet Explorer™ browser applications. The browser application 1210 requests hypertext web pages from the web server 1100 and renders the hypertext web pages on a display device for a user to view.

Client side code is also downloadable as applications on the client computing device 1200 and/or server 1100, in order to facilitate the operation of and/or interaction with the fingerprint recognition system and method therefor. Such applications could, for example, be downloaded from the Apple App Store™, Google Play™, or the like.

Client side code may also be provided as blockchain enabled code for suitable users of the system. Such blockchain enabled code may be configured for reading and writing directly to a node of the blockchain, or for communicating via a remote node such as a universal resolver node.

Client computing devices 1200 may communicate over the Internet 1300 via fixed line or wireless communication, for example using known networks of cellular communication towers 1400.

Computing Device

Figure 2:
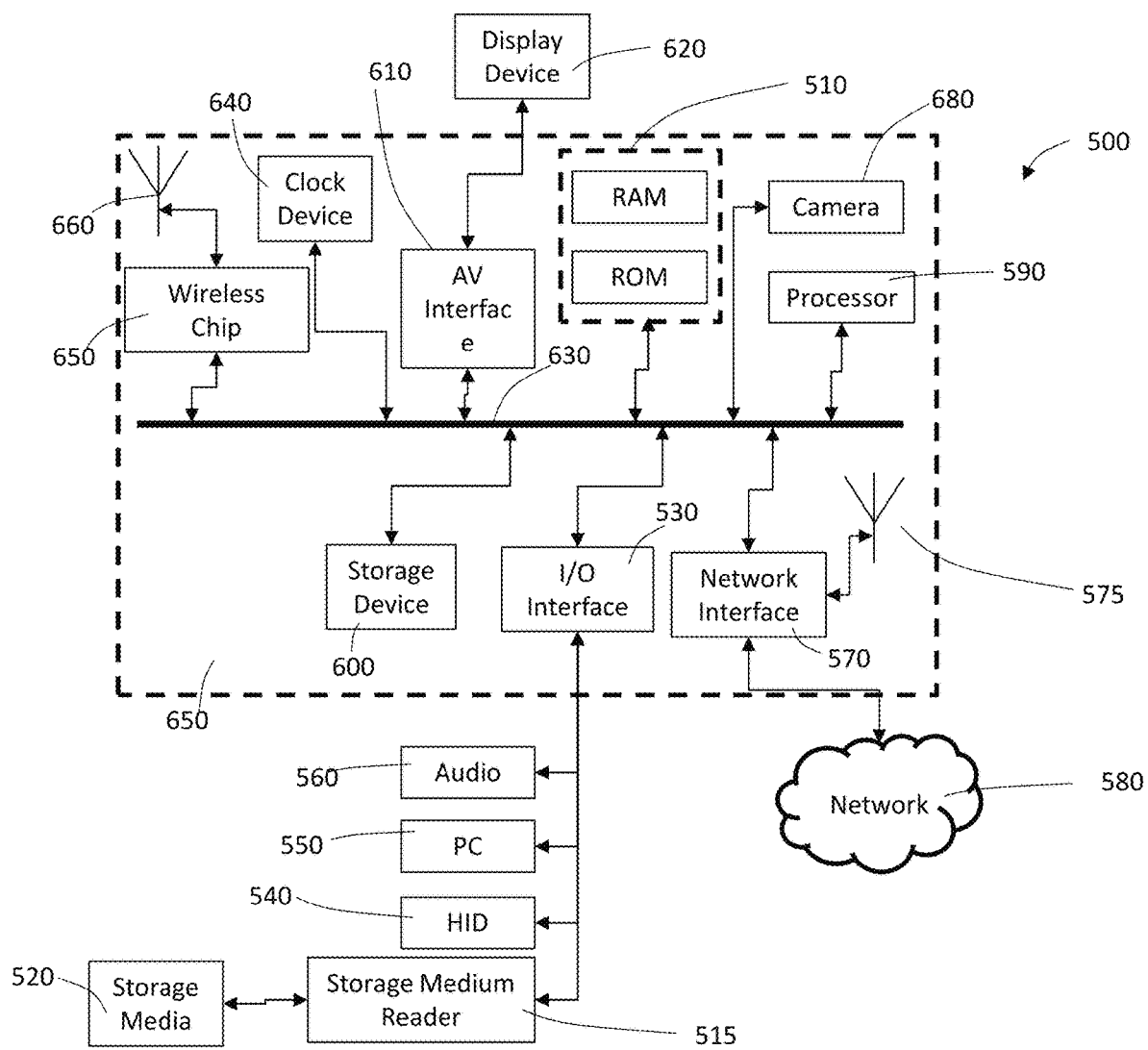
FIG. 2 shows a computing device on which the various embodiments described herein may be implemented in accordance with an embodiment of the present invention.

FIG. 2 shows a computing device 500. In a preferred embodiment, the computing device 500 takes the form of a server 1100 as described above. In this manner, the computing device 500 is adapted to comprise functionality for communication with the Internet 1300, storage capability (such as the database 1140) for storing user account data, records of communications, and the like.

However, it should be noted that the computing device 500 may be adapted for use as the client computing devices 1200 as is also shown in FIG. 1. In this manner, the computing device 500 may comprise differing technical integers in order to achieve the functionality as set out below.

In other words, the technical integers of the computing device 500 as shown in FIG. 2 are exemplary only and variations, adaptations and the like may be made thereto within the purposive scope of the embodiments described herein and having regard for the particular application of the computing device 500.

In particular the steps of the fingerprint recognition system and method therefor, as described in further detail below, can be implemented as computer program code instructions executable by the computing device 500.

The computer program code instructions may be divided into one or more computer program code instruction libraries, such as dynamic link libraries (DLL), wherein each of the libraries performs a one or more steps of the method. Additionally, a subset of the one or more of the libraries may perform graphical user interface tasks relating to the steps of the method.

The computing device 500 preferably comprises semiconductor memory 510 comprising volatile memory such as random access memory (RAM) or read only memory (ROM). The memory 510 may comprise either RAM or ROM or a combination of RAM and ROM.

The device further comprises I/O interface 530 for communicating with one or more peripheral devices. The I/O interface 530 may offer both serial and parallel interface connectivity. For example, the I/O interface 530 may comprise a Small Computer System Interface (SCSI), Universal Serial Bus (USB) or similar I/O interface for communication with one or more human input devices (HID) 540 such as keyboards, pointing devices, joysticks and the like.

The I/O interface 530 may also comprise an audio interface 560 for communicate audio signals to one or more audio devices, such as a speaker or a buzzer.

The device 500 also comprises a network interface 570 for communicating with one or more computer networks 580, such as the Internet 1300. The network 580 may be a wired network, such as a wired Ethernet™ network or a wireless network, such as a Bluetooth™ network or IEEE 802.11 network. The network 580 may be a local area network (LAN), such as a home or office computer network, or a wide area network (WAN), such as the Internet or private WAN. The device 500 can also include an antenna 575 configured for wireless communication with network 580.

The device 500 comprises an arithmetic logic unit or processor 590 for performing the computer program code instructions. The processor 590 may be a reduced instruction set computer (RISC) or complex instruction set computer (CISC) processor or the like. The computing device 500 further comprises a storage device 600, such as a magnetic disk hard drive or a solid state disk drive for storing data and/or software instructions.

Computer program code instructions may be loaded into the storage device 600 from the network 580 using network interface 570. Alternatively, computer program code instructions may be loaded into the storage device 600 from an online resource via the network 580 and network interface 570.

During the bootstrap phase, an operating system and one or more software applications are loaded from the storage device 600 into the memory 510. During the fetch-decode-execute cycle, the processor 590 fetches computer program code instructions from memory 510, decodes the instructions into machine code, executes the instructions and stores one or more intermediate results in memory 510.

In this manner, the instructions stored in the memory 510, when retrieved and executed by the processor 590, configures the computing device 500 as a special-purpose machine that may perform the functions described herein.

The computing device 500 can also include an audio/video interface 610 for conveying video signals to a display device 620, such as a liquid crystal display (LCD), light emitting diode (LED) display, organic light emitting diode (OLED) display, cathode-ray tube (CRT) or similar display device.

The device 500 preferably includes a communication bus subsystem 630 for interconnecting the various devices described above. The bus subsystem 630 may offer parallel connectivity such as Industry Standard Architecture (ISA), conventional Peripheral Component Interconnect (PCI) and the like or serial connectivity such as PCI Express (PCIe), Serial Advanced Technology Attachment (Serial ATA) and the like. The computing device 500 can also include a clock device 640 configured for providing accurate time stamps for use by the processor 590.

Preferably the client computing device that is operable by a user of the fingerprint recognition system and method therefor will by a mobile device such as a mobile phone, laptop, tablet or similar device and may have a near field communications (NFC) chip 650 installed, which may operate in conjunction with a suitable NFC antenna 660 in order to transmit and receive signals using the NFC protocol. Such an NFC chip 650 and antenna 660 can receive NFC or similar electromagnetic signals from similarly equipped devices. In alternative embodiments it is envisage that alternative protocols may be used where NFC is mentioned in describing the functionality below, such as Bluetooth™, or any of the IEEE802.11 protocols.

It is further anticipated that the computing device can include a physical random number generator 670. However, in alternative embodiments it is envisaged that the random number generator may be provided as part of a software module.

Lastly, it is anticipated that the computing device 500 can include a camera 680. The camera can be used to scan and/or input documents. The camera can be used to take photographs of fingerprints. The camera 680 may be connected via the I/O interface 530 or may be built into the computing device.

Fingerprint Recognition System and Method Therefor

Figure 13:
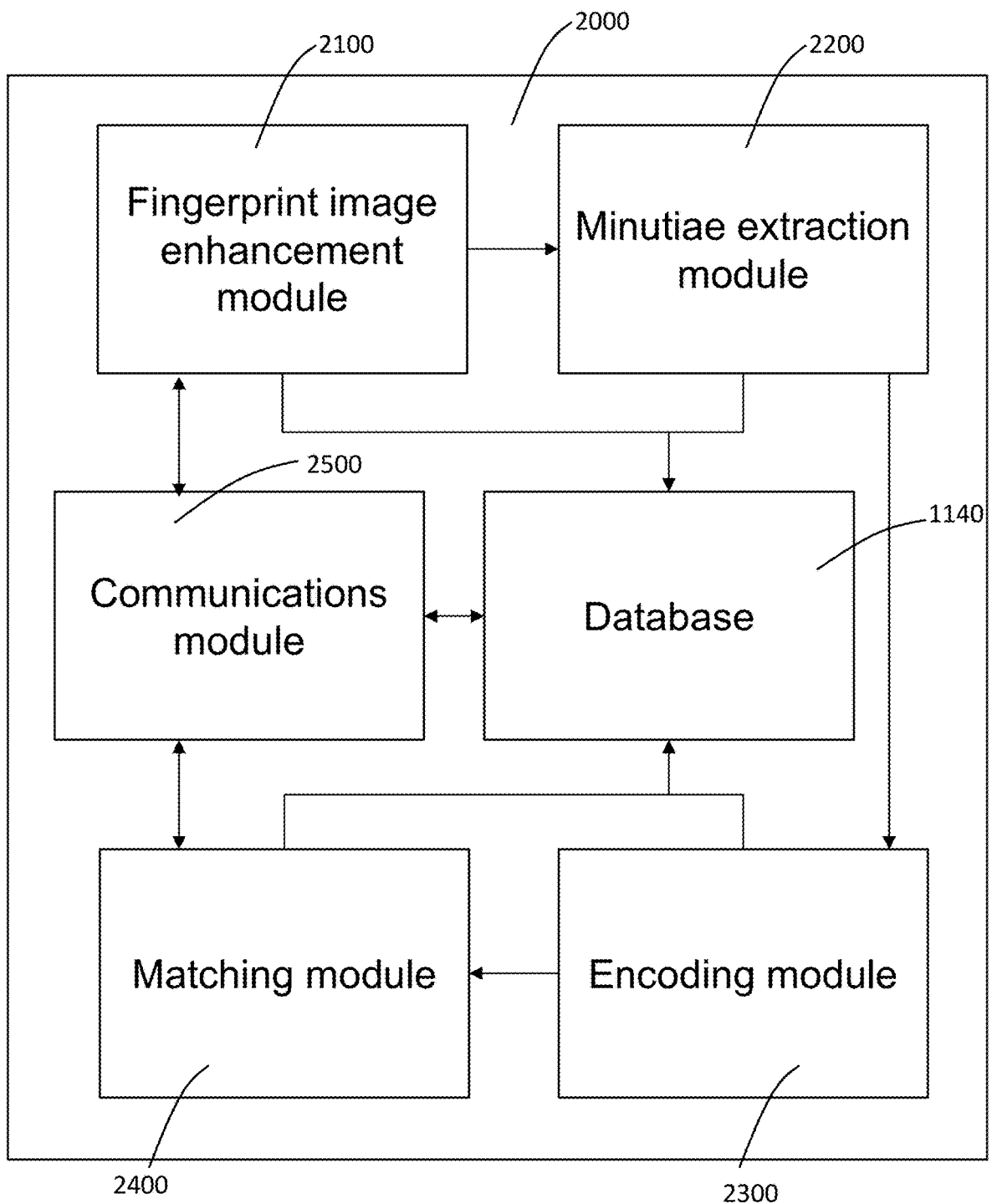
FIG. 13 shows a schematic view of a fingerprint recognition system showing modules.

An embodiment of the software modules of a fingerprint recognition system 2000 is shown in FIG. 13, showing a schematic diagram of the software modules.

Now referring to FIG. 13, the fingerprint recognition system 2000 includes a fingerprint image enhancement module 2100. The fingerprint image enhancement module 2100 is configured for enhancing at least one or more fingerprint images, whether the fingerprint images are received as candidate images, or as template images.

The fingerprint recognition system 2000 further includes a minutiae extraction module 2200 that is configured for extracting minutia features from the enhanced fingerprint images.

The fingerprint recognition system 2000 further includes an encoding module 2300 configured for encoding the extracted minutia features extracted from fingerprint images as a digital finger code.

The fingerprint recognition system 2000 further includes a matching module 2400 for matching template fingerprint images to candidate finger code that is associated with candidate fingerprint images that have been processed using the fingerprint recognition system.

In one embodiment, the fingerprint recognition system includes a communications module 2500 that is configured for receiving and/or transmitting data, including receiving images of fingerprints, and results of fingerprint matches.

Functionality

The functionality of the various embodiments described above will now be explained with reference to the flowcharts shown in FIGS. 8-12. In a discussion of the functionality below, communications between parties are preferably over a secure communication network.

Figure 3:
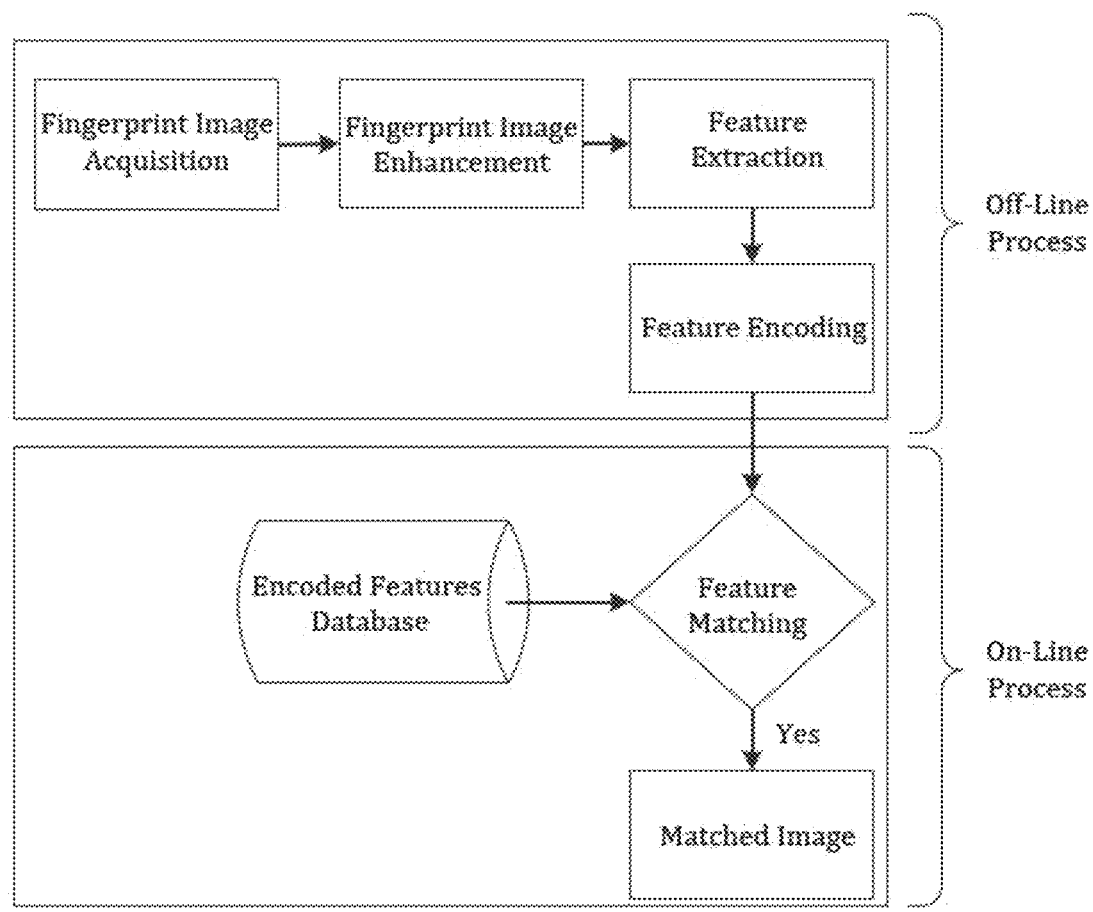
FIG. 3 shows a schematic diagram of a process for matching fingerprints.
Figure 8:
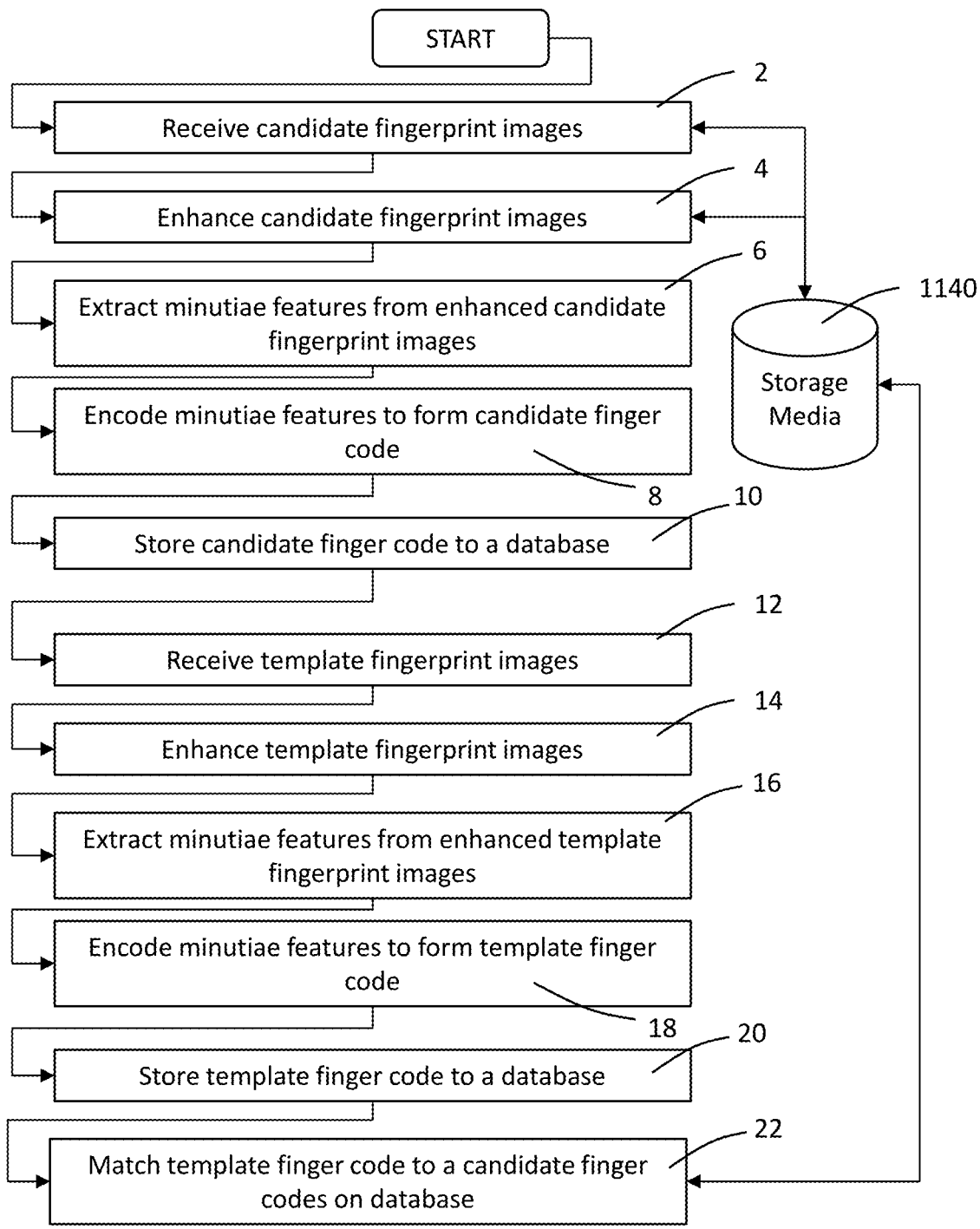
FIG. 8 shows a flow chart setting out a methodology for processing and matching fingerprints.

The proposed fingerprint identification algorithm consists of two main phases as shown in FIGS. 3 and 8. The first phase, which is offline, involves receiving 2 at least one or more fingerprint images, enhancing 4 the fingerprint images, extracting 6 minutiae features from the enhanced fingerprint images, and encoding 8 the extracted minutia features to generate a candidate finger code.

This step is performed once for all images in the database and stored 10 to create an encoded candidate database 1140.

The second phase, an online process, includes receiving 12 a new template image from a sensor, such as a camera, enhancing 14 the received new template image as an enhanced template image, extracting 16 minutiae features from the enhanced template image, and encoding 18 the extracted minutia features as a template finger code. The template finger code may also be stored 20. The template finger code is then matched against the candidate finger codes stored on the database 1140 from the first phase.

Fingerprint Enhancement

Figure 9:
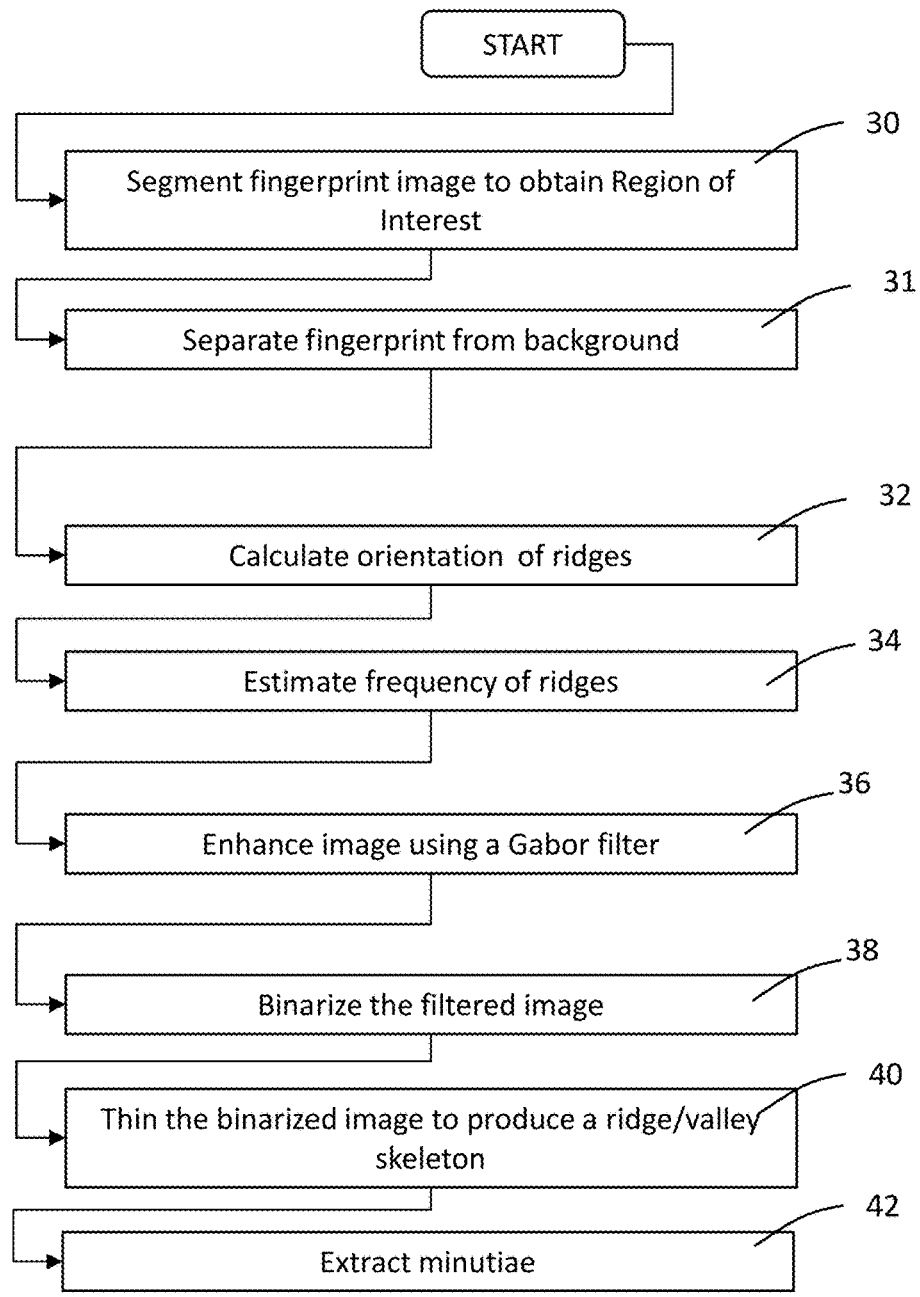
FIG. 9 shows a flow chart setting out a methodology for enhancing a fingerprint image.

In the proposed enhancement algorithm and as illustrated in FIG. 9, the initial step involves segmenting 30 the fingerprint image from the background to obtain the region of interest (ROI). After this the orientation of the ridges in the region of interest is calculated 32. In addition, the frequency of the ridges in the region of interest is estimated 34. To enhance the ridge/valley structure, Gabor-based contextual filtering 36 is applied, which utilizes local ridge frequency and orientation information. The filtered fingerprint image is then binarized 38 and thinned 40 to produce a ridge/valley skeleton. A quality mask is created to extract 42 high-quality minutiae features from the thinned image. Local ridge curvature, determined from local ridge orientations, helps estimate the region's quality. This process selects a limited number of high-quality minutiae features, leading to accurate fingerprint identification and reduced computational complexity during feature matching. The output is a quality-based minutiae list, which is encoded for identification purposes.

To enhance a fingerprint image, the first step is to obtain the region of interest (ROI), separating 31 the useful fingerprint region from the background. This segmentation is performed using the average magnitude of the gradient, which is higher in the foreground and lower in the background. After segmenting or extracting 30 the ROI, local ridge orientations and frequencies are calculated 32, which are necessary for Gabor-based enhancement. The most common method for calculating local ridge orientations involves gradient calculation. The proposed algorithm uses a method where ridge directions are computed using the inverse tangent of the gradient in both horizontal and vertical directions. The result of this step is an orientation image denoted by $O_{x,y}$, which contains the local ridge angles at each point (x, y) of the fingerprint image.

Once the ridge directions are calculated 32, the next step is to estimate 34 the local ridge frequencies. Estimating ridge frequency can be challenging due to the presence of scars and broken ridges at minutiae locations. In order to estimate 34 the ridge frequency, the fingerprint image, sized (M×N), is divided into B blocks of size (b×b). Each block is rotated by the angle $O_{m,n}$ to align the ridges vertically, where m and n are the block indices in the horizontal and vertical directions, respectively. Each block is then divided into S equal segments, and the vertical projection of each segment is computed. The frequency of each segment is determined by counting the number of peaks and dividing by the distance between the first and last peak. The dominant frequency of each block is calculated using alpha-trimmed mean filtering from the S segment frequencies. This approach provides accurate local ridge frequency estimations even in the presence of high ridge curvature.

After calculating the local ridge frequencies and orientations, the fingerprint image can be enhanced using Gabor filters. The enhancement method involves convolving each point of the fingerprint image with a Gabor filter tuned to the local ridge orientations and frequencies. The proposed algorithm generates a set of Gabor filters for a range of discretized frequencies and orientations present in the fingerprint image. Each pixel in the fingerprint image is then enhanced using a Gabor filter whose frequency and orientation are closest to the pixel's frequency $f_P$ and its orientation $\theta_P$, as described by Eq. 1.

$$g(x, y : \theta_p, f_p) = \exp\left[-\frac{1}{2}\left(\frac{x_{\theta_p}^2}{\sigma_x^2} + \frac{y_{\theta_p}^2}{\sigma_y^2}\right)\right]\cos(2\pi f_p x_{\theta_p}) \quad (1)$$

$$x_{\theta_p} = x\cos(\theta_p) + y\sin(\theta_p) \quad (2)$$

$$y_{\theta_p} = -x\sin(\theta_p) + y\cos(\theta_p) \quad (3)$$

where σx and σy are the standard deviations of the Gaussian envelope along the x and y axes, respectively.

The resulting enhanced image is then converted into a ridge/valley skeleton to facilitate the extraction of minutiae features. To achieve this skeletonization, the enhanced image undergoes binarization and thinning. Binarization involves converting the enhanced image into a binary image by classifying all pixels as either ones or zeros based on a selected threshold.

Figure 4:
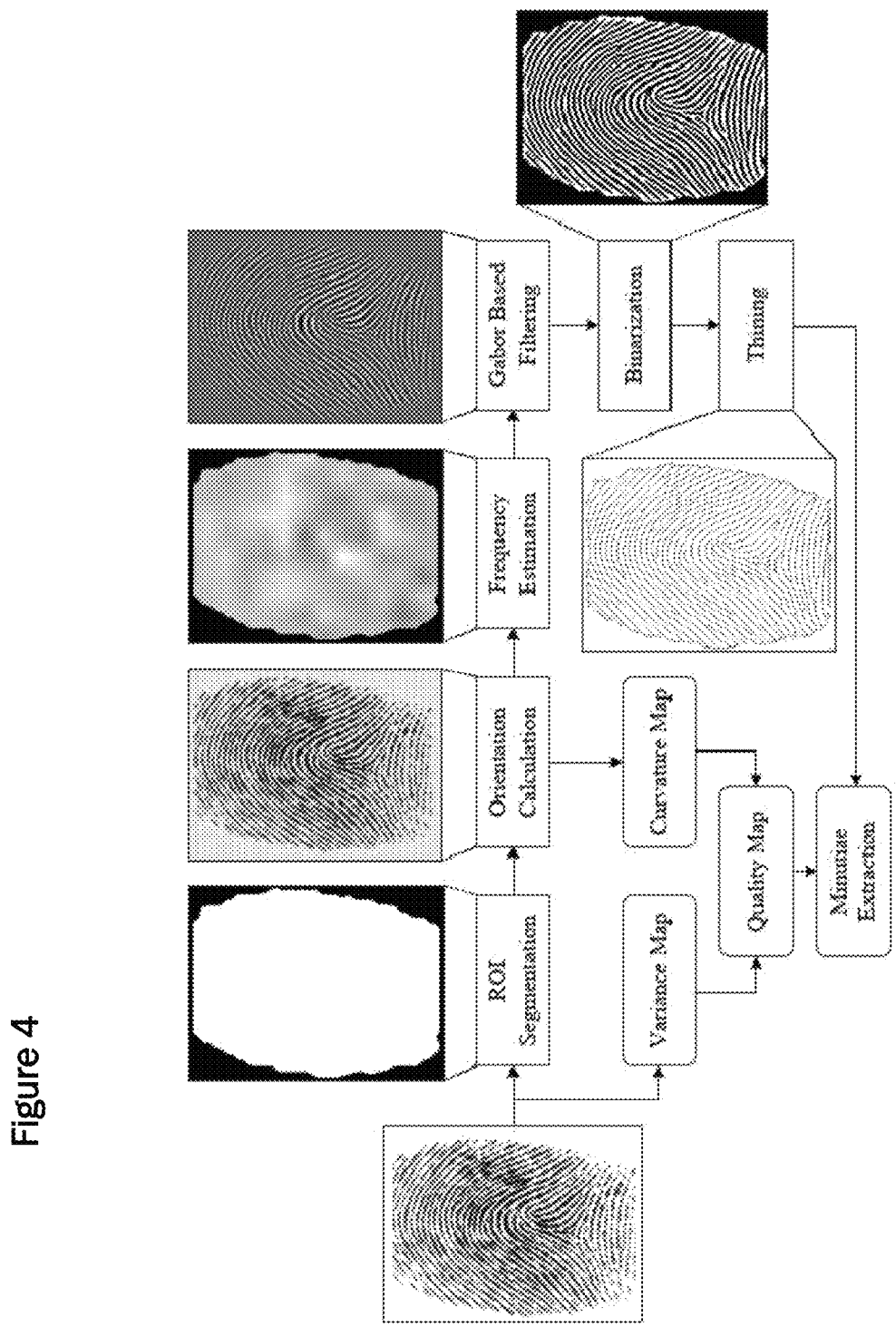
FIG. 4 shows an illustrated schematic diagram of a process for enhancing fingerprint images.

The binarized image is then thinned to reduce the ridge width to a single pixel, enabling reliable extraction of minutiae features. The most commonly used minutiae features are ridge endings and bifurcations, which can be easily extracted from the thinned fingerprint image. FIG. 4 illustrates the results of the enhancement steps and their visual representation on a sample fingerprint image from the FVC2002-DB1A database. Before extracting these minutiae features, a quality mask is created and used in conjunction with the thinned image to extract minutiae from high-quality regions.

Feature Extraction

Fingerprint images encompass various features crucial for fingerprint matching, such as ridges, singular points (core points), and minutiae. The most reliable feature for fingerprint matching is the minutia point, (first observed by Sir Francis Galton based on the discontinuities in local ridge patterns and hence termed "Galton details"). Each minutia point possesses its location. Ridge endings and ridge bifurcations are primarily used for fingerprint identification due to their stability and accurate detection compared to other minutiae types. Moreover, all other minutiae points can be understood as combinations of ridge endings and bifurcations, obviating the need to detect them separately. These minutiae points are typically extracted from thinned fingerprint images. However, thinning algorithms may introduce noise in the ridge pattern, leading to the detection of spurious minutiae.

To extract candidate minutiae points, a local neighborhood of each pixel is scanned 50 within a 3×3 window. A ridge pixel is classified 52 based on the number of transitions from 0 to 1 that occur during the scanning of the 8 neighboring pixels of a candidate minutia in a clockwise direction. A pixel is identified as a ridge bifurcation if there are 3 transitions from 0 to 1, whereas a pixel is classified as a ridge ending if only one transition from 0 to 1 is detected.

After minutiae feature extraction is carried out, false minutiae are removed 54, and a minutiae list is generated 56. Each minutia point is represented by its location and dominant angle.

Feature Encoding

Figure 10:
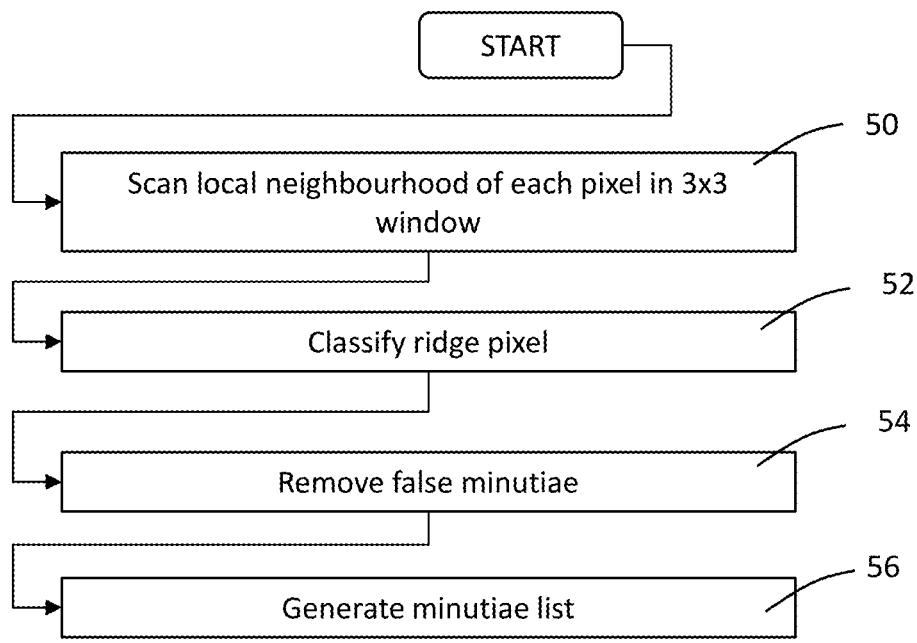
FIG. 10 shows a flow chart setting out a methodology for feature extraction from a fingerprint image.
Figure 11:
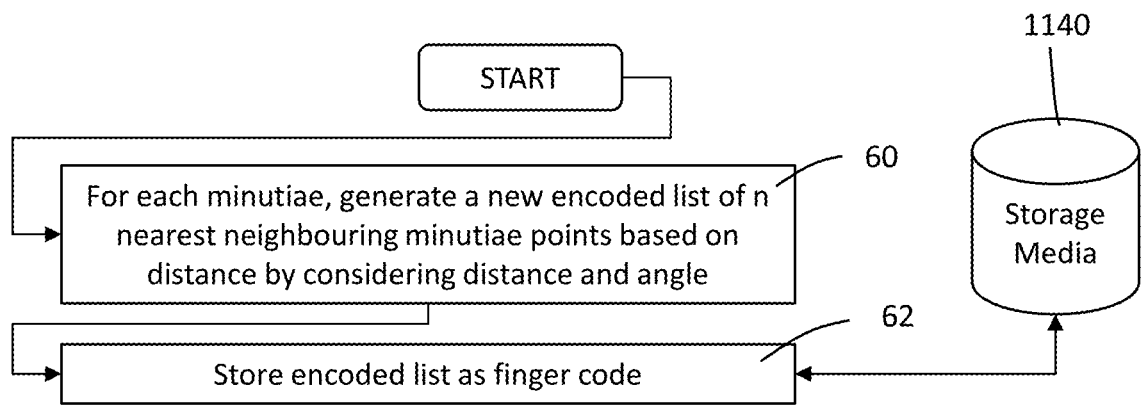
FIG. 11 shows a flow chart setting out a methodology for encoding features extracted from a fingerprint image.
Figure 12:
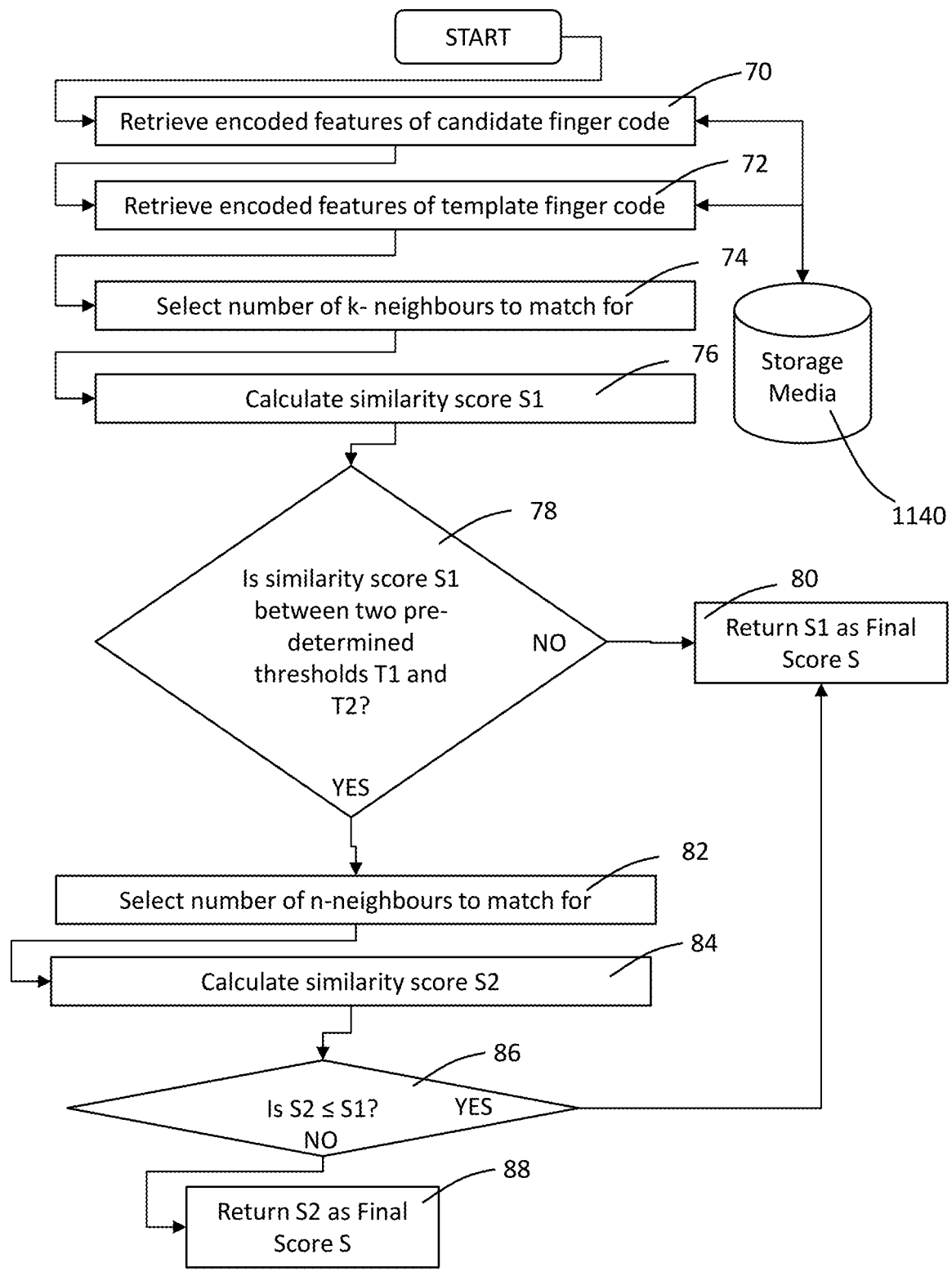
FIG. 12 shows a flow chart setting out a methodology for matching the minutia of a template finger code to a candidate finger code.

Now described with reference to FIG. 10, once the feature extraction from the fingerprint image is completed, the features encoding process is initiated. In this stage, each minutia point is selected as a reference point and encoded based on its neighboring minutiae. The following procedure is typically employed to encode a fingerprint image:

a. For each minutia point minutia ($M_i$) from the minutiae list ($M_L$), where i is the index of the reference minutia point.

i. Based on the Euclidean distance between minutia ($M_i$) and all other minutiae in minutiae list ($M_L$), create a new list ($M_i^{Nearest}$) of n nearest neighboring minutiae points, excluding the reference minutia ($M_i$) itself. This can be expressed as follows:

$$M_i^{Nearest}(x_k, y_k, \theta_k) = M_L(x_j, y_j, \theta_j) \quad (4)$$

Where k=1:n iterates through the indices of the nearest minutia points, and j represents the index of each nearest minutia point from minutiae list ($M_L$).

ii. An encoded list of minutiae, denoted as ($m_i$), is generated 60 by considering the relative distance and angle ($\rho i, \theta_i, \phi_i$) features between the focal minutia ($M_i$) and its neighboring minutiae ($M_i^{Nearest}$) The features ($\rho i, \theta i, \phi i$) for each minutia are computed as given in Eq. (5-7).

$$\rho_j = \sqrt{dx_j^2 + dy_j^2} \quad (5)$$

$$\theta_j = \tan^{-1}\left(\frac{dy_j}{dx_j}\right) \quad (6)$$

$$\phi_j = M_L(3 \times (i-1) + 2) - M_i^{Nearest}(3 \times (j-1) + 2) \quad (7)$$

where, $$dx_j = M_L(3 \times (i-1)) - M_i^{Nearest}(3 \times (j-1)) \quad (8)$$

$$dy_j = M_L(3 \times (i-1) + 1) - M_i^{Nearest}(3 \times (j-1) + 1) \quad (9)$$

The encoding of the minutia ($m_i$) involves a combination of features ($\rho j, \theta j, \phi j$) derived from the n nearest neighboring minutiae, excluding the reference minutia itself, as outlined in above step.

b. The final encoded minutiae list ($M_L^{Encoded}$) for a given fingerprint comprises a combination of all individual minutia encodings $m_i$, represented in Equation. 10.

$$M_L^{Encoded} = m_1, m_2, m_3, \ldots, m_N \tag{10}$$

where N is the number of minutiae points in a given fingerprint image.

c. The encoded minutiae list ($M_L^{Encoded}$) is stored 62 in the database as a candidate finger-code (C).

Feature Matching

In fingerprint matching, the template finger code $F^T$ of an input fingerprint image is generated uniquely for each candidate fingerprint. This template finger code is then compared with all available candidate finger codes $F^C$ stored in the database to identify the corresponding fingerprint image. The candidate finger code from the database that yields the highest similarity score with the template finger-code is deemed to be the match for the template fingerprint image. To determine the similarity score between a candidate finger-code $F^C$ and the template finger-code $F^T$, an exhaustive point pattern search algorithm is utilized. This algorithm matches each minutia $m_i$ from the template finger code with every minutia $m_j$ in the candidate finger code.

An exhaustive search algorithm is necessary to perform the matching process because the order of occurrence of minutiae is uncertain, particularly in cases involving spurious or missing neighboring minutiae. The similarity score between the template finger code and the candidate finger code is determined by calculating a ($S_{Matrix}$). This matrix serves as an accumulator ($Acc_{i,j}$) for every minutia pair, as outlined in equations (11-13) below.

$$\text{Sim} = 100 \times \left( \frac{M_{mat}^{pair}}{\min(M, N)} \right) \tag{11}$$

where $M_{mat}^{pair}$ is the matched minutiae pair, M and N are the number of minutiae of the candidate and template images. $M_{mat}^{pair}$ is calculated as $$M_{mat}^{pair} = \sum_{i=1}^{N} \sum_{j=1}^{M} (S_{Matrix}(N \times (i-1) + (j-1))) \tag{12}$$

and $$S_{Matrix}(N \times (i-1) + (j-1)) = Acc_{i,j} \tag{13}$$

To match a minutia pair ($m_i$, $m_j$) from candidate and template minutiae, the encoded features (ρi, θi, ϕi) of candidate minutiae and (ρj, θj, ϕj) of template minutiae are compared, and their result is computed as $Acc_{i,j}$. If more than the threshold $T_N$ neighbors out of $n^2$ neighbors are matched, then the minutia pair ($m_i$, $m_j$) is considered matched, as outlined in equation 14 below.

$$Acc_{i,j} \begin{cases} 1, & \text{if } \left( \sum_{k=1}^{n^2} D_{i,j}(k) \right) \geq T_N \\ 0, & \text{otherwise} \end{cases} \tag{14}$$

Minutia encoding is conducted on its n neighbors, hence matching one minutia pair ($m_i$, $m_j$) necessitates $n^2$ feature matches. The encoded features (ρi, ϕi, ϕi) of candidate minutiae and (ρj, θj, ϕj) of template minutiae are compared by computing $D_{i,j}(k)$, which calculates the differences between the features of ($m_i$) and ($m_j$). If $D_{i,j}(k)$ is below a specified threshold, then the feature is deemed matched, as specified in equations (15-18).

$$D_{i,j}(k) = \begin{cases} 1, & \text{if } (T_\rho(i,j) \wedge T_\theta(i,j) \wedge T_\phi(i,j)) \\ 0, & \text{otherwise} \end{cases} \tag{15}$$

$$T_\rho(i,j) = \Delta \rho_{i,j}(k) \leq T_\rho \tag{16}$$

$$T_\theta(i,j) = \{(\Delta \theta_{i,j}(k) \leq T_\theta) \vee (\Delta \theta_{i,j}(k) \geq 180 - T_\theta)\} \tag{17}$$

$$T_\phi(i,j) = \{(\Delta \phi_{i,j}(k) \leq T_\theta) \vee (\Delta \phi_{i,j}(k) \geq 180 - T_\phi)\} \tag{18}$$

Where ($T_\rho$, $T_\theta$, and $T_\phi$) are distinct thresholds for features ($\rho_i$, $\theta_i$, and $\phi_i$), respectively. $\Delta\rho_{i,j}(k)$, $\Delta\theta_{i,j}(k)$, and $\Delta\phi_{i,j}(k)$ are computed as indicated in equations (19, 20, and 21), respectively.

$$\Delta \rho_{i,j}(k) = F^T \left( 3 \times \text{floor}\left( \frac{k-1}{n} \right) \right) - F^C(3 \times \text{mod}(n(k-1))) \tag{19}$$

$$\Delta \theta_{i,j}(k) = F^T \left( 3 \times \text{floor}\left( \frac{k-1}{n} \right) + 1 \right) - F^C(3 \times \text{mod}(n(k-1)) + 1) \tag{20}$$

$$\Delta \phi_{i,j}(k) = F^T \left( 3 \times \text{floor}\left( \frac{k-1}{n} \right) + 2 \right) - F^C(3 \times \text{mod}(n(k-1)) + 2) \tag{21}$$

Figure 5:
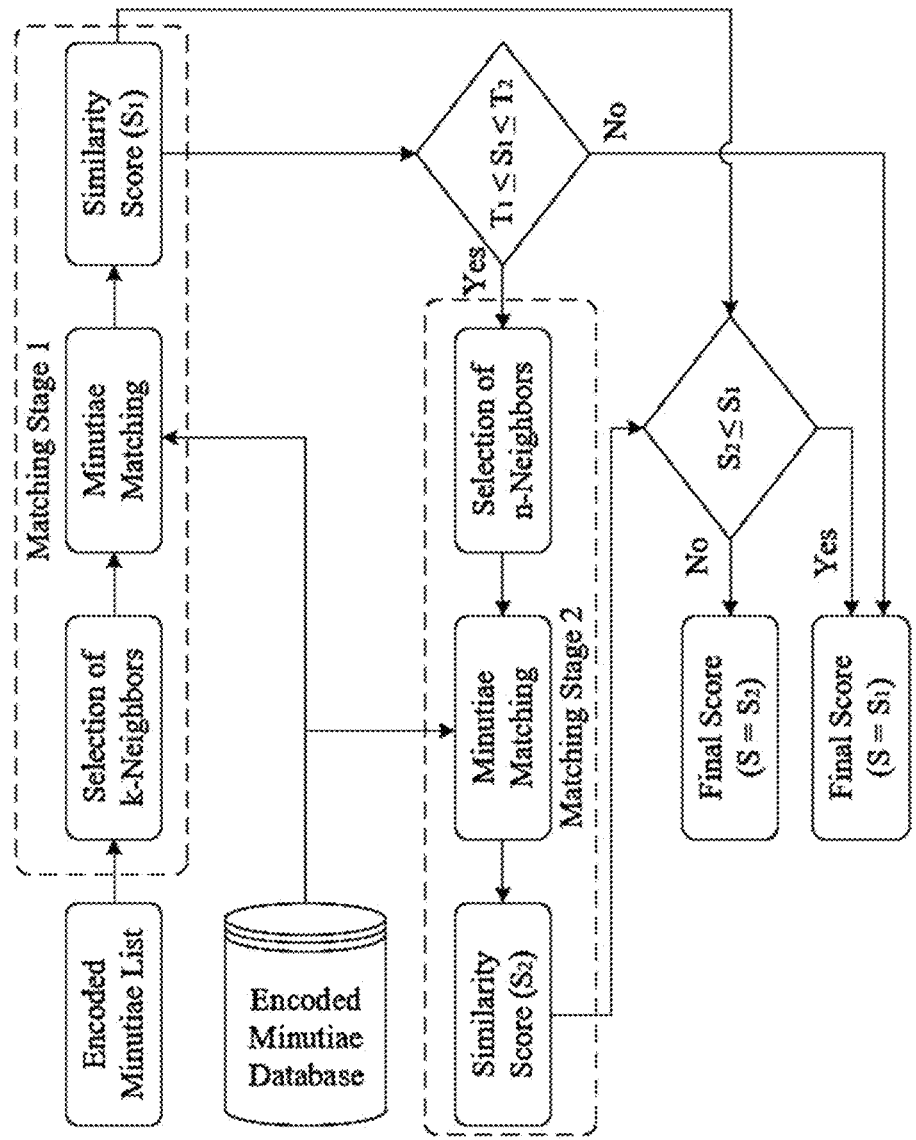
FIG. 5 shows a schematic diagram of a process for matching a candidate fingerprint image to a finger code candidate database.

As shown in FIGS. 5 and 8, it is anticipated that the minutia matching will preferably be carried out in two stages in a hierarchical matching algorithm. In a first stage, the encoded minutia list or features of the template finger code will be retrieved 70, as well as retrieving 72 the encoded minutia list or features of the candidate finger codes from the candidate finger code database 1140.

After this, a number of nearest neighbours k to match for will be selected 74. A similarity score $S_1$ will then be calculated 76. A determination 78 will then be made of whether the similarity score $S_1$ is between two predetermined thresholds $T_1$ and $T_2$.

If the similarity score $S_1$ does not fall between these two predetermined thresholds, then $S_1$ will be returned 80 as the final score S.

If the similarity score $S_1$ does fall between these two predetermined thresholds, then a second number of nearest neighbours n to match for, where (n>k), will be selected 82. A second similarity score $S_2$ will be calculated 84. A determination 86 will then be made as to whether $S_2$ is less than or equal to $S_1$. If $S_2$ is less than or equal to $S_1$, then $S_1$ will be returned 80 as the final score S. If $S_2$ is not less than or equal to $S_1$, then $S_2$ will be returned 88 as the final score S.

Examples and Results

Results of Minutiae Matching Stage The Fingerprint Verification Competition (FVC2002) DBI-A (Maio, D., Maltoni, D., Cappelli, R., Wayman, J. L., Jain, A. K.: Fvc2002: Second fingerprint verification competition. In: 2002 International conference on pattern recognition. vol. 3, pp. 811-814. IEEE (2002)) database is used for experiments. FVC testing protocol (see Maio, D., Maltoni, D., Cappelli, R., Wayman, J. L., Jain, A. K.: *Fvc2002: Second fingerprint verification competition. In: 2002 International conference on pattern recognition.* vol. 3, pp. 811-814. *IEEE* (2002)) is used for performance evaluation, where an equal error rate (ERR) performance indicator is used. The total number of fingerprint images (subjects) is 100, and each subject has 8 samples. For an Equal Error Rate (EER) calculation, the experiments are carried out in two stages, where the false non-matching rate (FNMR) and false matching rate (FMR) are computed. In the first stage, the false non-matching rate (FNMR), which is known as genuine matching, is computed by matching each sample of a subject (fingerprint) with the remaining samples of the same subject. In the second stage, the false matching rate (FMR), which is known as imposter matching, is computed by matching the first sample of each subject (fingerprint) with the first sample of the remaining subjects. The total number of genuine matching ($E_{genuine}$) and imposter matching ($E_{imposter}$) experiments is given in Eq. (22-23):

$$E_{genuine} = 100 \times \left(\frac{8 \times 7}{2}\right) = 2800 \quad (22)$$

$$E_{imposter} = \left(\frac{100 \times 99}{2}\right) = 4950 \quad (23)$$

EER is a measure of the system's performance, and it is given by either FMR or FNMR, at a point where both FMR and FNMR are equal (Maltoni, D., Maio, D., Jain, A. K., Prabhakar, S., et al.: *Handbook of fingerprint recognition*, vol. 2. *Springer* (2009)). Table 1 shows different EERs achieved based on the different numbers of matched neighbors, $T_N$ and the number of nearest k minutiae neighbors that are used in encoding of a given minutia code. Table 1 shows a complete empirical analysis of EER. It can be seen that as the number of neighbors k involved in encoding increases, the accuracy of the matching algorithm also increases. However, by increasing k the number of computations involved in matching increases, as well as the size of the finger code. It can be seen that a minimum EER of 1.56% is achieved for k=9 nearest neighbors and neighbor threshold $T_N=4$.

Table 2 shows different EERs achieved based on the different numbers of matched neighbors, $T_N$ and the number of nearest n minutiae neighbors that are used in the encoding of a given minutia code at stage two. It can be seen from Table 2 that a minimum EER of 0.05% is achieved for n=9 nearest neighbors and neighbor threshold $T_N=2$.

TABLE 2

EER comparisons of different n-nearest neighbors for different matched neighbors $T_N$ of stage 2.

| Matched Neighbors ($T_N$) | n-Nearest Neighbors | | | | |
|---|---|---|---|---|---|
| | 6 | 7 | 8 | 9 | 10 |
| 1 | 0.14 | 0.16 | 0.17 | 0.19 | 0.20 |
| 2 | 0.32 | 0.12 | 0.06 | 0.05 | 0.10 |
| 3 | 1.73 | 0.76 | 0.58 | 0.48 | 0.21 |
| 4 | 2.60 | 2.21 | 1.85 | 0.95 | 0.73 |
| 5 | 4.86 | 2.21 | 2.57 | 2.25 | 1.95 |
| 6 | 5.05 | 4.94 | 3.10 | 2.87 | 2.59 |
| 7 | — | 5.06 | 5.00 | 4.89 | 3.04 |
| 8 | — | — | 5.07 | 5.04 | 4.96 |
| 9 | — | — | — | 5.08 | 5.05 |
| 10 | — | — | — | — | 5.08 |

Figure 7:
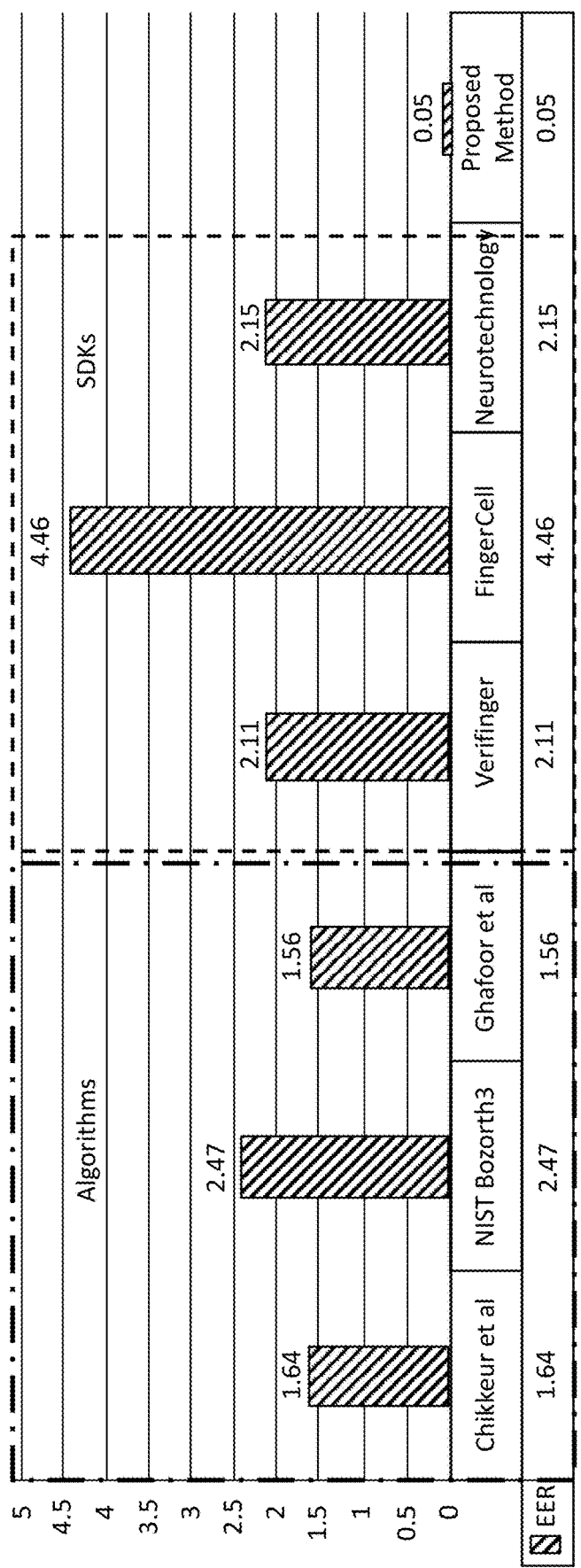
FIG. 7 shows a comparison of the proposed methodologies of the invention with previous studies and commercially available software development kits.

FIG. 7 presents the EER comparison of the proposed method with state-of-the-art matching algorithms (K-plet and coupled BFS proposed by Chikkerur et al. (Chikkerur, S., Cartwright, A. N., Govindaraju, V.: *K-plet and coupled bfs: a graph based fingerprint representation and matching algorithm. In: Advances in Biometrics: International Conference, ICB* 2006, Hong Kong, China, Jan. 5-7, 2006. *Proceedings.* pp. 309-315. *Springer* (2005) 11), NIST Bozorth3 (Watson, C. I., Garris, M. D., Tabassi, E., Wilson, C. L., McCabe, R. M., Janet, S., Ko, K.: *User's guide to. NIST Biometric Image Software*), and Ghafoor et al. (Ghafoor, M., Iqbal, S., Tariq, S. A., Taj, I. A., Jafri, N. M.: *Efficient fingerprint matching using gpu. IET Image Processing*

TABLE 1

EER comparisons of different k-nearest neighbors for different matched neighbors $T_N$.

| Matched Neighbors ($T_N$) | k-Nearest Neighbors | | | | | | | | | |
|---|---|---|---|---|---|---|---|---|---|---|
| | 1 | 2 | 3 | 4 | 5 | 6 | 7 | 8 | 9 | 10 |
| 1 | 17.7 | 18.27 | 19.29 | 22.21 | 23.98 | 27.2 | 29.81 | 32.25 | 33.51 | 36.35 |
| 2 | — | 6.52 | 3.87 | 3.77 | 3.75 | 4.1 | 4.66 | 5.34 | 6 | 7.46 |
| 3 | — | — | 6.73 | 3.59 | 2.25 | 1.73 | 1.77 | 2.04 | 2.16 | 2.33 |
| 4 | — | — | — | 11.19 | 4.09 | 2.36 | 1.89 | 1.68 | 1.56 | 1.57 |
| 5 | — | — | — | — | 17.37 | 7.11 | 3.14 | 2.01 | 1.84 | 1.98 |
| 6 | — | — | — | — | — | 22.17 | 10.72 | 5.4 | 3.27 | 2.26 |
| 7 | — | — | — | — | — | — | 76.64 | 14.39 | 8.19 | 5.14 |
| 8 | — | — | — | — | — | — | — | 80.82 | 18.64 | 10.55 |
| 9 | — | — | — | — | — | — | — | — | 83.77 | 22.17 |
| 10 | — | — | — | — | — | — | — | — | — | 85.89 |

Figure 6:
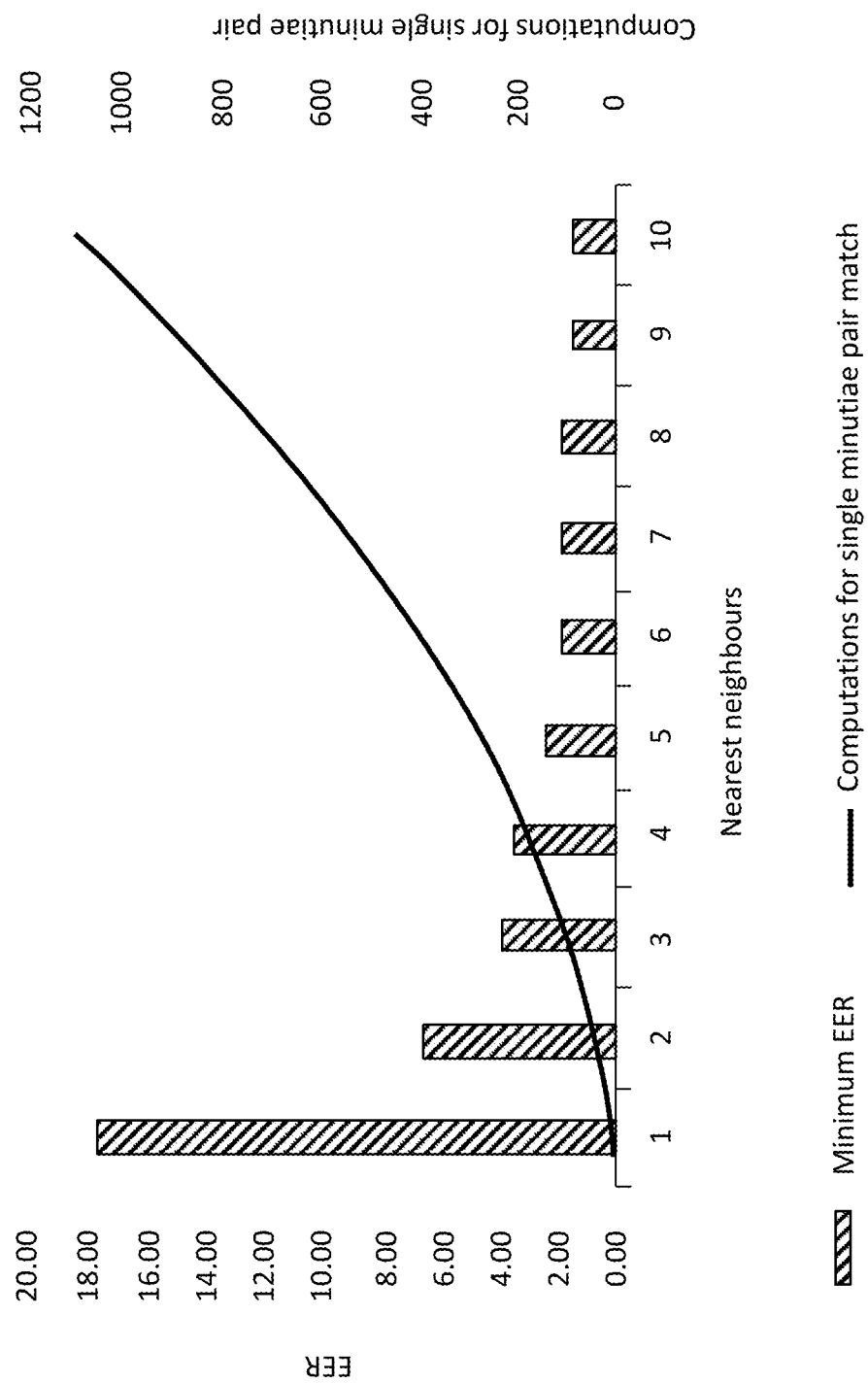
FIG. 6 shows a graphical representation between the minimum EER achieved for k-nearest neighbors in comparison to the computations required for a single minutiae pair match.

FIG. 6 shows a graphical representation between the minimum EER achieved for k-nearest neighbors in comparison to the computations required for a single minutiae pair match. It can be observed that after k=6 there is no significant improvement in the EER, but the computations increase considerably. Based on this analysis, six nearest neighbors (k=6) of each minutiae are chosen for encoding and matching, and the nearest matched neighbor threshold is kept at three ($T_N=3$) for efficient fingerprint matching implementation.

12(2), 274-284 (2018)) respectively. It is evident from FIG. 7 that the proposed method has outperformed all other methods in terms of EER by achieving 1.59%, 2.42%, and 1.51% times better EER than the K-plet and coupled BFS proposed by Chikkerur et al., NIST Bozorth3, and Ghafoor et al., respectively. The proposed method is also compared with known fingerprint Software Development Kits (SDKs) and outperformed these in terms of EER by achieving 2.06%, 4.41%, and 2.1% times better EER than the Veri-Finger, FingerCell, and Neurotechnology, respectively.

In this study, we introduced a solution for fingerprint identification. The primary objective of the enhancement was to improve the clarity of pertinent details while mitigating noise artifacts within fingerprint images, thus improving the accuracy of identification. Once the fingerprint image is enhanced, the proposed method uses minutiae extraction, followed by the minutiae encoding stage. After that, a hierarchical minutiae matching algorithm with adaptive nearest neighbors was employed. Finally, the experimental findings validate the significant superiority of the proposed approach to fingerprint enhancement and matching. The proposed hierarchical minutiae matching algorithm achieved a minimum EER of 0.05% on the FVC2002 DB-1A dataset.

Interpretation

Unless otherwise defined, all terms (including technical and scientific terms) used herein have the same meaning as commonly understood by one of ordinary skill in the art to which this invention belongs. It will be further understood that terms used herein should be interpreted as having a meaning that is consistent with their meaning in the context of this specification and the relevant art and will not be interpreted in an idealized or overly formal sense unless expressly so defined herein. For the purposes of the present invention, additional terms are defined below. Furthermore, all definitions, as defined and used herein, should be understood to control over dictionary definitions, definitions in documents incorporated by reference, and/or ordinary meanings of the defined terms unless there is doubt as to the meaning of a particular term, in which case the common dictionary definition and/or common usage of the term will prevail.

The terminology used herein is for the purpose of describing particular embodiments only and is not intended to be limiting of the invention. As used herein, the singular articles "a", "an" and "the" are intended to include the plural forms as well, unless the context clearly indicates otherwise and thus are used herein to refer to one or to more than one (i.e. to "at least one") of the grammatical object of the article. By way of example, the phrase "an element" refers to one element or more than one element.

The term "about" is used herein to refer to quantities that vary by as much as 30%, preferably by as much as 20%, and more preferably by as much as 10% to a reference quantity. The use of the word 'about' to qualify a number is merely an express indication that the number is not to be construed as a precise value.

Throughout this specification, unless the context requires otherwise, the words "comprise", "comprises" and "comprising" will be understood to imply the inclusion of a stated step or element or group of steps or elements but not the exclusion of any other step or element or group of steps or elements.

The term "real-time" for example "displaying real-time data," refers to the display of the data without intentional delay, given the processing limitations of the system and the time required to accurately measure the data.

As used herein, the term "exemplary" is used in the sense of providing examples, as opposed to indicating quality. That is, an "exemplary embodiment" is an embodiment provided as an example, as opposed to necessarily being an embodiment of exemplary quality for example serving as a desirable model or representing the best of its kind.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Bus

In the context of this document, the term "bus" and its derivatives, while being described in a preferred embodiment as being a communication bus subsystem for interconnecting various devices including by way of parallel connectivity such as Industry Standard Architecture (ISA), conventional Peripheral Component Interconnect (PCI) and the like or serial connectivity such as PCI Express (PCIe), Serial Advanced Technology Attachment (Serial ATA) and the like, should be construed broadly herein as any system for communicating data.

In Accordance with:

As described herein, 'in accordance with' may also mean 'as a function of' and is not necessarily limited to the integers specified in relation thereto.

Composite Items

As described herein, 'a computer implemented method' should not necessarily be inferred as being performed by a single computing device such that the steps of the method may be performed by more than one cooperating computing devices.

Similarly objects as used herein such as 'web server', 'server', 'client computing device', 'computer readable medium' and the like should not necessarily be construed as being a single object, and may be implemented as a two or more objects in cooperation, such as, for example, a web server being construed as two or more web servers in a server farm cooperating to achieve a desired goal or a computer readable medium being distributed in a composite manner, such as program code being provided on a compact disk activatable by a license key downloadable from a computer network.

Database:

In the context of this document, the term "database" and its derivatives may be used to describe a single database, a set of databases, a system of databases or the like. The system of databases may comprise a set of databases wherein the set of databases may be stored on a single implementation or span across multiple implementations. The term "database" is also not limited to refer to a certain database format rather may refer to any database format. For example, database formats may include MySQL, MySQLi, XML or the like.

Wireless:

The invention may be embodied using devices conforming to other network standards and for other applications, including, for example other WLAN standards and other wireless standards. Applications that can be accommodated include IEEE 802.11 wireless LANs and links, and wireless Ethernet.

In the context of this document, the term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some embodiments they might not. In the context of this document, the term "wired" and its derivatives may be used to describe circuits, devices, systems, methods, techniques, communications channels, etc., that may communicate data through the use of modulated electromagnetic radiation through a solid medium. The term does not imply that the associated devices are coupled by electrically conductive wires.

Processes:

Unless specifically stated otherwise, as apparent from the following discussions, it is appreciated that throughout the specification discussions utilizing terms such as "processing", "computing", "calculating", "determining", "analysing" or the like, refer to the action and/or processes of a computer or computing system, or similar electronic computing device, that manipulate and/or transform data represented as physical, such as electronic, quantities into other data similarly represented as physical quantities.

Processor:

In a similar manner, the term "processor" may refer to any device or portion of a device that processes electronic data, e.g., from registers and/or memory to transform that electronic data into other electronic data that, e.g., may be stored in registers and/or memory. A "computer" or a "computing device" or a "computing machine" or a "computing platform" may include one or more processors.

The methodologies described herein are, in one embodiment, performable by one or more processors that accept computer-readable (also called machine-readable) code containing a set of instructions that when executed by one or more of the processors carry out at least one of the methods described herein. Any processor capable of executing a set of instructions (sequential or otherwise) that specify actions to be taken are included. Thus, one example is a typical processing system that includes one or more processors. The processing system further may include a memory subsystem including main RAM and/or a static RAM, and/or ROM.

Computer-Readable Medium:

Furthermore, a computer-readable carrier medium may form, or be included in a computer program product. A computer program product can be stored on a computer usable carrier medium, the computer program product comprising a computer readable program means for causing a processor to perform a method as described herein.

Networked or Multiple Processors:

In alternative embodiments, the one or more processors operate as a standalone device or may be connected, e.g., networked to other processor(s), in a networked deployment, the one or more processors may operate in the capacity of a server or a client machine in server-client network environment, or as a peer machine in a peer-to-peer or distributed network environment. The one or more processors may form a web appliance, a network router, switch or bridge, or any machine capable of executing a set of instructions (sequential or otherwise) that specify actions to be taken by that machine.

Note that while some diagram(s) only show(s) a single processor and a single memory that carries the computer-readable code, those in the art will understand that many of the components described above are included, but not explicitly shown or described in order not to obscure the inventive aspect. For example, while only a single machine is illustrated, the term "machine" shall also be taken to include any collection of machines that individually or jointly execute a set (or multiple sets) of instructions to perform any one or more of the methodologies discussed herein.

Additional Embodiments

Thus, one embodiment of each of the methods described herein is in the form of a computer-readable carrier medium carrying a set of instructions, e.g., a computer program that are for execution on one or more processors. Thus, as will be appreciated by those skilled in the art, embodiments of the present invention may be embodied as a method, an apparatus such as a special purpose apparatus, an apparatus such as a data processing system, or a computer-readable carrier medium. The computer-readable carrier medium carries computer readable code including a set of instructions that when executed on one or more processors cause a processor or processors to implement a method. Accordingly, aspects of the present invention may take the form of a method, an entirely hardware embodiment, an entirely software embodiment or an embodiment combining software and hardware aspects. Furthermore, the present invention may take the form of carrier medium (e.g., a computer program product on a computer-readable storage medium) carrying computer-readable program code embodied in the medium.

Carrier Medium:

The software may further be transmitted or received over a network via a network interface device. While the carrier medium is shown in an example embodiment to be a single medium, the term "carrier medium" should be taken to include a single medium or multiple media (e.g., a centralized or distributed database, and/or associated caches and servers) that store the one or more sets of instructions. The term "carrier medium" shall also be taken to include any medium that is capable of storing, encoding or carrying a set of instructions for execution by one or more of the processors and that cause the one or more processors to perform any one or more of the methodologies of the present invention. A carrier medium may take many forms, including but not limited to, non-volatile media, volatile media, and transmission media.

Blockchain

A blockchain is a collection of information that is stored electronically in blocks on one or more computer systems, the blocks storing sets of information and being chained onto a previously filled block, forming a chain of data known as the blockchain. New information that follows a freshly added block is compiled into a newly formed block that will also be added to the chain and preferably time stamped once the block is filled. Blockchains are typically implemented as a decentralized, distributed network, in which a plurality of nodes of the network are synchronized to store the same blockchain information.

Implementation

It will be understood that the steps of methods discussed are performed in one embodiment by an appropriate processor (or processors) of a processing (i.e., computer) system executing instructions (computer-readable code) stored in storage. It will also be understood that the invention is not limited to any particular implementation or programming technique and that the invention may be implemented using any appropriate techniques for implementing the functionality described herein. The invention is not limited to any particular programming language or operating system.

Means for Carrying Out a Method or Function

Furthermore, some of the embodiments are described herein as a method or combination of elements of a method that can be implemented by a processor of a processor device, computer system, or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

Connected

Similarly, it is to be noticed that the term connected, when used in the claims, should not be interpreted as being limitative to direct connections only. Thus, the scope of the expression a device A connected to a device B should not be limited to devices or systems wherein an output of device A is directly connected to an input of device B. It means that there exists a path between an output of A and an input of B which may be a path including other devices or means.

"Connected" may mean that two or more elements are either in direct physical or electrical contact, or that two or more elements are not in direct contact with each other but yet still co-operate or interact with each other.

Embodiments

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the above description of example embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description of Specific Embodiments are hereby expressly incorporated into this Detailed Description of Specific Embodiments, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Specific Details

In the description provided herein, numerous specific details are set forth. However, it is understood that embodiments of the invention may be practiced without these specific details. In other instances, well-known methods, structures and techniques have not been shown in detail in order not to obscure an understanding of this description.

It will be appreciated that the methods/apparatus/devices/systems described/illustrated above at least substantially provide a fingerprint recognition system and method therefor.

The fingerprint recognition system and method therefor described herein, and/or shown in the drawings, are presented by way of example only and are not limiting as to the scope of the invention. Unless otherwise specifically stated, individual aspects and components of the fingerprint recognition system and method therefor may be modified, or may have been substituted therefore known equivalents, or as yet unknown substitutes such as may be developed in the future or such as may be found to be acceptable substitutes in the future. The fingerprint recognition system and method therefor may also be modified for a variety of applications while remaining within the scope and spirit of the claimed invention, since the range of potential applications is great, and since it is intended that the present invention be adaptable to many such variations.

Terminology

In describing the preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar technical purpose. Terms such as "forward", "rearward", "radially", "peripherally", "upwardly", "downwardly", and the like are used as words of convenience to provide reference points and are not to be construed as limiting terms.

Different Instances of Objects

As used herein, unless otherwise specified the use of the ordinal adjectives "first", "second", "third", etc., to describe a common object, merely indicate that different instances of like objects are being referred to, and are not intended to imply that the objects so described must be in a given sequence, either temporally, spatially, in ranking, or in any other manner.

Combinations of Features in Embodiments

Different features are described in different embodiments in this specification, however it is envisaged that any features shown in any embodiment described may be used with any other features in any other embodiment in any combination, unless this is not logically possible.

Comprising and Including

In the claims which follow and in the preceding description of the invention, except where the context requires otherwise due to express language or necessary implication, the word "comprise" or variations such as "comprises" or "comprising" are used in an inclusive sense, i.e. to specify the presence of the stated features but not to preclude the presence or addition of further features in various embodiments of the invention.

Any one of the terms: including or which includes or that includes as used herein is also an open term that also means including at least the elements/features that follow the term, but not excluding others. Thus, including is synonymous with and means comprising.

Scope of Invention

Thus, while there has been described what are believed to be the preferred embodiments of the invention, those skilled in the art will recognize that other and further modifications may be made thereto without departing from the spirit of the invention, and it is intended to claim all such changes and modifications as fall within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

Although the invention has been described with reference to specific examples, it will be appreciated by those skilled in the art that the invention may be embodied in many other forms.

Chronological Order

For the purpose of this specification, where method steps are described in sequence, the sequence does not necessarily mean that the steps are to be carried out in chronological order in that sequence, unless there is no other logical manner of interpreting the sequence.

Markush Groups

In addition, where features or aspects of the invention are described in terms of Markush groups, those skilled in the art will recognise that the invention is also thereby described in terms of any individual member or subgroup of members of the Markush group.

INDUSTRIAL APPLICABILITY

It is apparent from the above, that the arrangements described are applicable to the crime and insurance industries.

The invention claimed is:

1. A fingerprint recognition system for recognizing fingerprints, the fingerprint recognition system including:
   a. a processor operatively configured for executing digital instructions;
   b. digital storage media operatively connected to the processor and configured for storing instructions configured for directing the processor to carry out:
      receiving at least one or more candidate fingerprint images;
      extracting minutia features from the at least one or more candidate fingerprint images;
      encoding the minutia features extracted from the candidate fingerprint image as a candidate finger code for each candidate fingerprint image;
      receiving a template fingerprint image;
      extracting minutia features from the template fingerprint images;
      encoding the fingerprint minutia features extracted from the template fingerprint as a template finger code;
      in a first matching step, matching the template finger code against at least one or more candidate finger codes by
         selecting a first number k of adjacent minutiae to match for around a minutiae;
         comparing the encoded features of each minutiae and k adjacent minutiae of the template finger code to each minutiae and k adjacent minutiae of a candidate finger code;
         calculating a first similarity score $S_1$ based on the comparison;
      wherein if the first similarity score $S_1$ is larger than or equal to a predetermined first threshold value $T_1$ and smaller than or equal to a predetermined second threshold value $T_2$ ($T_1 \leq S_1 \leq T_2$), in a second matching step, matching the template finger code against at least one or more candidate finger codes by
         selecting a second number n of adjacent minutiae to match for around a minutiae, where the second number n is larger than the first number k;
         comparing the encoded features of each minutiae and n adjacent minutiae of the template finger code to the encoded features of each minutiae and n adjacent minutiae of a candidate finger code; and calculating a second similarity score $S_2$ based on the comparison.

2. The fingerprint recognition system as claimed in claim 1, wherein the instructions are configured for directing the processor to:
   select a fingerprint region of interest of one or more selected from the candidate fingerprint images and the template fingerprint images; and
   enhance the one or more selected from the candidate fingerprint images and the template fingerprint image by separating the fingerprint region of interest from the background as a separated fingerprint.

3. The fingerprint recognition system as claimed in claim 2, wherein the instructions are configured for directing the processor to:
   calculate local ridge orientations and frequencies of the separated fingerprint.

4. The fingerprint recognition system as claimed in claim 2, wherein the instructions are configured for directing the processor to:
   enhance the separated fingerprint using Gabor filters to generate an enhanced image by convolving each pixel of the separated fingerprint with a Gabor filter tuned to the calculated local ridge orientations and frequencies.

5. The fingerprint recognition system as claimed in claim 4, wherein the instructions are configured for directing the processor to:
   convert the enhanced image into a binary image by classifying all pixels in the enhanced image as either once or zeros based on a selected threshold;
   thin the binary image to reduce a ridge width to a single pixel:
   scan a local region of each pixel including each adjacent pixel; and
   classify the ridge pixel as a minutia based on the number of transitions from 0 to 1 that occurred during the scanning of the adjacent pixels.

6. The fingerprint recognition system as claimed in claim 5, wherein the instructions are configured for directing the processor to:
   encode each minutia point based on its adjacent minutia, with the minutia point being the reference.

7. The fingerprint recognition system as claimed in claim 6, wherein the instructions are configured for directing the processor to:
   generate an encoded list of minutiae using relative distance and angle between a reference minutia and a neighboring minutiae; and
   store the encoded minutia list as a finger code in a candidate database.

8. A method of recognizing fingerprints, the method being carried out on an electronic device and including:
   receiving at least one or more candidate fingerprint images;
   extracting minutia features from each of the candidate fingerprint images;
   encoding the minutia features extracted from the candidate fingerprint image as a candidate finger code for each candidate fingerprint-image;
   receiving an image of a template fingerprint as a template image;
   extracting minutia features from the enhanced template images;
   encoding the fingerprint minutia features extracted from the template fingerprint as a template finger code;
   in a first matching step, matching the template finger code against at least one or more candidate finger codes by
   selecting a first number k of adjacent minutiae to match for around a minutiae;
   comparing the encoded features of each minutiae and k adjacent minutiae of the template finger code to the encoded features of each minutiae and k adjacent minutiae of a candidate finger code;
   calculating a first similarity score $S_1$ based on the comparison;
   wherein if the first similarity score $S_1$ is between a predetermined pair of threshold values $T_1$ and $T_2$, in a second matching step, matching the template finger code against at least one or more candidate finger codes by
   selecting a second number n of adjacent minutiae to match for around a minutiae, where the second number n is larger than the first number k;
   comparing the encoded features of each minutiae and n adjacent minutiae of the template finger code to the encoded features of each minutiae and n adjacent minutiae of a candidate finger code; and
   calculating a second similarity score $S_2$ based on the comparison.

9. The method as claimed in claim 8, wherein the method includes:
   selecting a fingerprint region of interest of one or more selected from the candidate fingerprint images and the template fingerprint image; and
   enhancing the one or more selected from the candidate fingerprint images and the template fingerprint image by separating the fingerprint region of interest from the background as a separated fingerprint.

10. The method as claimed in claim 9, wherein the method includes:
    calculating local ridge orientations and frequencies of the separated fingerprint.

11. The method as claimed in claim 10, wherein the method includes:
    enhancing the separated fingerprint using Gabor filters to generate an enhanced image by convolving each pixel of the separated fingerprint with a Gabor filter tuned to the calculated local ridge orientations and frequencies.

12. The method as claimed in claim 11, wherein the method includes:
    converting the enhanced image into a binary image by classifying all pixels in the enhanced image as either once or zeros based on a selected threshold; and
    thinning the binary image to reduce the ridge width to a single pixel.

13. The method as claimed in claim 12, wherein the method includes:
    scanning a local region of each pixel including each adjacent pixel; and
    classifying the ridge pixel as a minutia based on the number of transitions from 0 to 1 that occurred during the scanning of the adjacent pixels.

14. The method as claimed in claim 13, wherein the method includes:
    creating a list of n neighboring minutia points to a reference minutia, excluding the reference minutia itself, based on the Euclidean distance between the reference minutia and a minutia list.

15. A fingerprint recognition system for recognizing fingerprints, the fingerprint recognition system including:
    a fingerprint image enhancement module configured for enhancing at least one or more fingerprint images;

a minutiae extraction module configured for extracting minutia features from the enhanced fingerprint images; and an encoding module configured for encoding the fingerprint extracted minutia features as a digital finger code, and a matching module configured for in a first matching step, matching a template finger code against at least one or more candidate finger codes by selecting a first number k of adjacent minutiae to match for around a minutiae;

comparing the encoded features of each minutiae and k adjacent minutiae of the template finger code to the encoded features of each minutiae and k adjacent minutiae of a candidate finger code;

calculating a first similarity score $S_1$ based on the comparison;

wherein if the first similarity score $S_1$ is between a predetermined pair of threshold values $T_1$ and $T_2$, in a second matching step, matching the template finger code against at least one or more candidate finger codes by selecting a second number n of adjacent minutiae to match for around a minutiae, where the second number n is larger than the first number k;

comparing the encoded features of each minutiae and n adjacent minutiae of the template finger code to the encoded features of each minutiae and n adjacent minutiae of a candidate finger code; and calculating a second similarity score $S_2$ based on the comparison.

16. The fingerprint recognition system as claimed in claim 1, wherein the instructions are configured for directing the processor to:

finalize the first similarity score $S_1$ as the final similarity score S if the similarity score is not between the predetermined pair of threshold values $T_1$ and $T_2$;

finalize the second similarity score $S_2$ as final similarity score S if the second similarity score $S_2$ is higher than the first similarity score $S_1$; and finalize the first similarity score $S_1$ as final similarity score S if the second similarity score $S_2$ is lower than or equal to the first similarity score $S_1$.

17. The method as claimed in claim 8, wherein the method includes:

finalizing the first similarity score $S_1$ as the final similarity score S if the similarity score is not between the predetermined pair of threshold values $T_1$ and $T_2$;

finalizing the second similarity score $S_2$ as final similarity score S if the second similarity score $S_2$ is higher than the first similarity score $S_1$; and finalizing the first similarity score $S_1$ as final similarity score S if the second similarity score $S_2$ is lower than or equal to the first similarity score $S_1$.

18. The fingerprint recognition system as claimed in claim 15, wherein the matching module is configured for:

finalizing the first similarity score $S_1$ as the final similarity score S if the similarity score is not between the predetermined pair of threshold values $T_1$ and $T_2$;

finalizing the second similarity score $S_2$ as final similarity score S if the second similarity score $S_2$ is higher than the first similarity score $S_1$; and finalizing the first similarity score $S_1$ as final similarity score S if the second similarity score $S_2$ is lower than or equal to the first similarity score $S_1$.

* * * * *